(12) United States Patent
Eisenberger et al.

(10) Patent No.: US 9,747,652 B2
(45) Date of Patent: Aug. 29, 2017

(54) PROVIDING CONTROLLED LEVELS OF COLLABORATIVE EXCHANGE OF DATA FOR REGISTERED PARTICIPATING SUBSCRIBERS AND PUBLISHERS

(75) Inventors: George Eisenberger, Somers, NY (US); Edgar H McCulloch, III, Washington, DC (US); Thomas L. Richards, II, Chicaco, IL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1695 days.

(21) Appl. No.: 12/817,779

(22) Filed: Jun. 17, 2010

(65) Prior Publication Data
US 2010/0256994 A1 Oct. 7, 2010

Related U.S. Application Data

(63) Continuation of application No. 11/032,391, filed on Jan. 10, 2005, now Pat. No. 7,827,234.

(51) Int. Cl.
G06F 13/00 (2006.01)
G06Q 50/22 (2012.01)
G06Q 10/10 (2012.01)
G06Q 50/24 (2012.01)

(52) U.S. Cl.
CPC .......... G06Q 50/22 (2013.01); G06Q 10/10 (2013.01); G06Q 10/101 (2013.01); G06Q 50/24 (2013.01)

(58) Field of Classification Search
USPC ........................................................ 709/203
See application file for complete search history.

(56) References Cited

U.S. PATENT DOCUMENTS

2005/0010442 A1* 1/2005 Kragh .............................. 705/2
2006/0155578 A1* 7/2006 Eisenberger et al. ............. 705/2

FOREIGN PATENT DOCUMENTS

JP 2002-108709 A 4/2002
JP 2003-141262 A 5/2003

* cited by examiner

Primary Examiner — Robert B Harrell
(74) Attorney, Agent, or Firm — Steven L. Nichols; Fabian VanCott

(57) ABSTRACT

Methods, systems and related computer products for providing entitlement controlled levels of collaborative exchange of data using a computer network of Subscribers and Publishers, are configured to: (a) define a set of different privacy levels, each privacy level having associated data sharing parameters that control a participating Publisher's ability to send and a participating Subscriber's ability to receive content specific data; and (b) provide an electronic privacy level register that defines the different data sharing parameters for each of the different privacy levels and identifies an associated at least one privacy level for each participating Subscriber and Publisher.

16 Claims, 29 Drawing Sheets

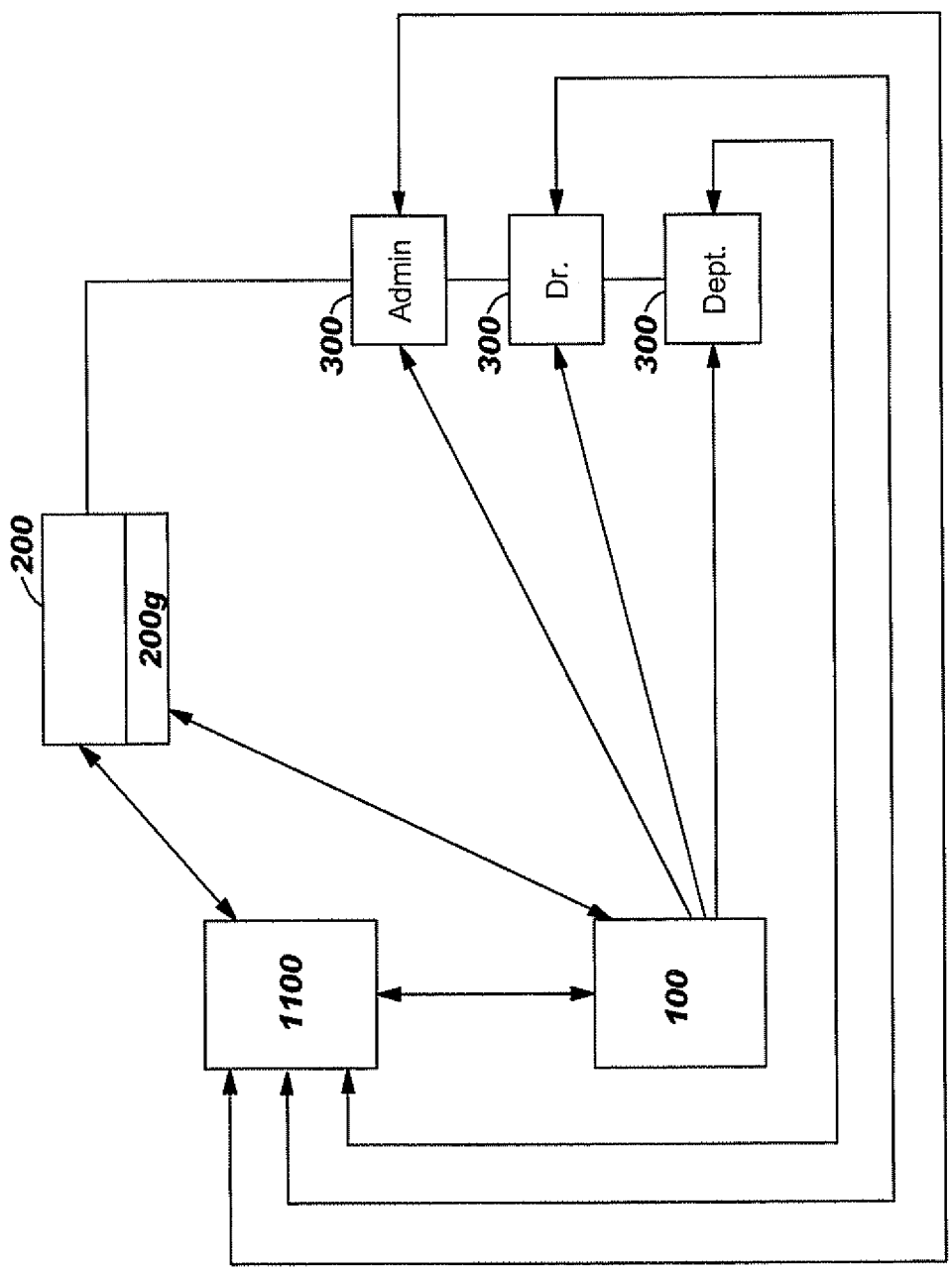

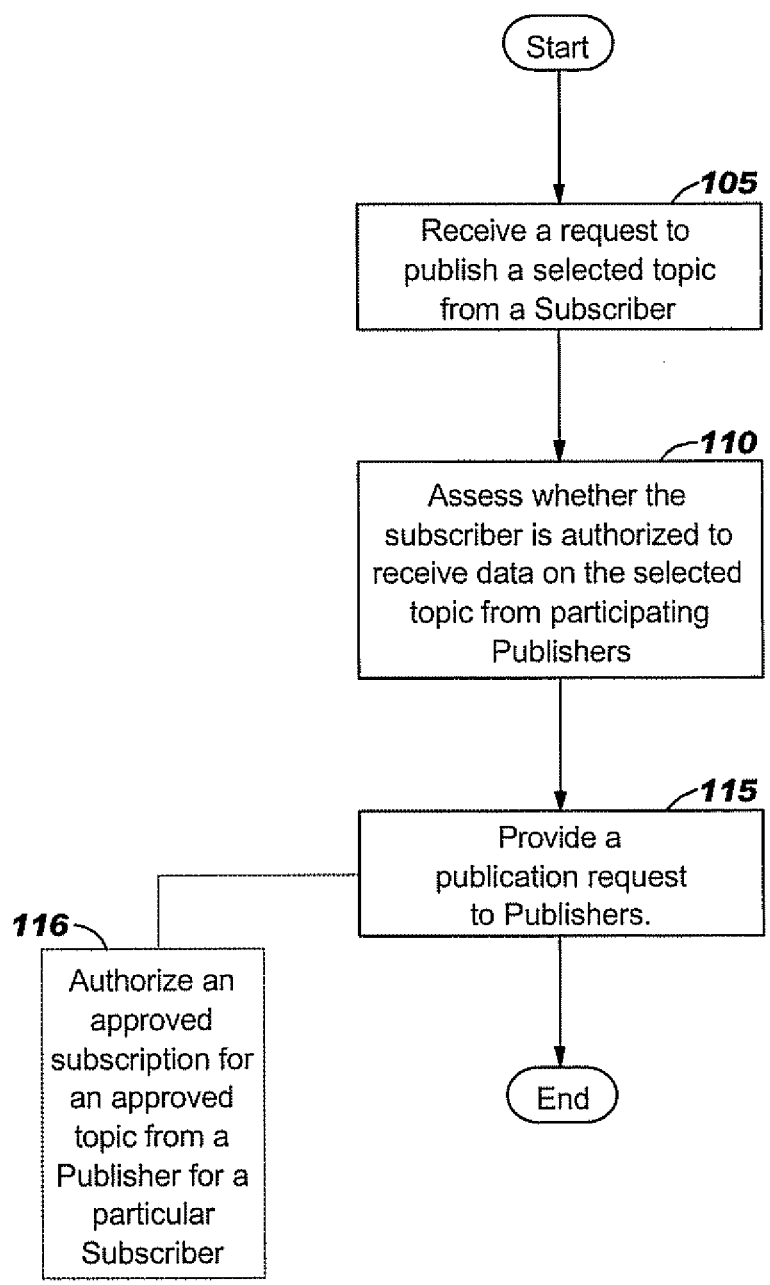

Sample Data Flow Summary - Aggregate Messages by Date

FIG. 13

Sample HCN Message includes Labs, Pharmacy, and Diagnosis Records for Patient

200m

Message submitted successfully for publication:
Submission time: YYYY-DY-MO 12:25:09 09.921
Publisher ID: 'Provider 1'
Publish Topic: 'Stroke Diagnosis'
Rule Name: 'Stroke Diagnosis'
Patient ID: '123153'
Message Timestamp: 'YYYY-DY-MOT12:26:17-07:00'

200p
```
'MSH|^~\&|<XXX>||20030719084337||ORU^R01|<XXX>|<XXX>|2.4|
PID|||123153^^^&Provider 1|<XXX>||<XXX>|F|||||||<XXX>|
PV1|||<XXX>|||<XXX>|<XXX>|||HNA|||<XXX>|<XXX>|||||<XXX>||||||<XXX>|
ORC|NW|100|18491559|SC||^QD&0900^INDEF^20030719090000^^R^0||20030719090839|^^^|<XXX>|<XXX>|<XXX>|<XXX>|
RXE|0000429160^PANTOPRAZOLE EC TAB 40 MG^L[40]|^MG|TABLET EC||||1|EA|
RXR|^ORAL|'
```

200l
```
'MSH|^~\&|<XXX>||20030719084337||ORU^R01|<XXX>|<XXX>|2.4|
PID|||123153^^^&Provider 1|<XXX>||<XXX>|F|||||||<XXX>|
OBR|||T44676BCBLUD037F^1|600-7^LOINC^BLOOD
CULTURE|||20030715160000||||||<XXX>|<XXX>|<XXX>|||||<XXX>|P|^^^^^R|<XXX>|
OBX|1|TX|36484^BLUD^MED|0|SPECIMEN DESCRIPTION: BLOOD|||||F|
OBX|2|TX|60187^NGB4^MED|0|CULTURE: NO GROWTH OF BACTERIA OR FUNGI AFTER 4 DAYS|||||F|'
```

200d
```
'MSH|^~\&|HIHLS21-215259|EAGLE 2000|||20030731200333||ADT^A08|20030727024001798320|P|2.3|||NE|NE|
EVN|A08|<XXX>||<XXX>|<XXX>|
PID|<XXX>||123153^^^&Provider 1|<XXX>|<XXX>|<XXX>|F|<XXX>|<XXX>|<XXX>|<XXX>|<XXX>|<XXX>|
DG1|<XXX>||9|430^SUBARACHNOID HEMORRHAGE^19|<XXX>|<XXX>|A|<XXX>|<XXX>|<XXX>||||<XXX>|
DG1|<XXX>||9|430^SUBARACHNOID HEMORRHAGE^19|<XXX>|<XXX>|<XXX>|P|
DG1|<XXX>||9|401.9^HYPERTENSION NOS^19|<XXX>|<XXX>|S|
DG1|<XXX>||9|307.9^SPECIAL SYMPTOM NEC/NOS^19|<XXX>|<XXX>|S|
', 'MSH|^~\&|<XXX>|<XXX>|||20030723190145||ADT^A03|<XXX>|<XXX>|2.3|||<XXX>|<XXX>|<XXX>|
EVN|A03|<XXX>||<XXX>|<XXX>|
PID|<XXX>||123153^^^&Provider 1|<XXX>|<XXX>|<XXX>|F|<XXX>|<XXX>|<XXX>|<XXX>|<XXX>|<XXX>|
```

FIG. 14

Sample view of notifications on the HCN Portal

Healthcare Collaboration Network
File  Edit  View  Favorites  Tools  Help
◀ Back ▶  ⊗  □  ⌂  Search  Address [          ]  Go  Links  Google  Hotmail  PDC - W3 hcn
Healthcare Collaboration Network
Welcome:  Publisher  Role: [Publisher ▼] [Change Role]    • home  • help
                                                          • contact us  • log out
                                                          • legal        IBM

Publications | Publication Requests | Authorization Requests | Health Topics | HCN Notifications | Participants

NHCN Notifications
Click on a subject title to view the Notification Details.

| Date | Time | Type | From | Subject |
|---|---|---|---|---|
| 03/26/YY | 12:00 | Email | Administrator | System Unavailable |
| 03/25/YY | 13:25 | Information | Administrator | Publication added to topic Anthrax |
| 03/25/YY | 15:44 | Information | "A" General Hospital | New Health Topic Diabetes has been added |
| 03/24/YY | 10:27 | Email | "A" General Hospital | New Health Topic Diabetes has been added |
| 03/23/YY | 11:11 | System | "A" General Hospital | New Health Topic Diabetes has been added |
| 03/23/YY | 16:03 | System | "A" General Hospital | New Health Topic Diabetes has been added |

→ more NHCN notifications

Publications                                                [Create Publication]
Display Publications:
● All publications
○ Containing the word: [          ]  [Display]
                                                → more publications

Publication Requests
The following table lists subscriber requests for publications

| Topic Name | Requesting Organization |
|---|---|
| Accutane with no pregnancy test | FDA |
| ADR for Accutane | FDA |
| ADR for Accutane | Centers for Medicare and Medicaid |

→ more publication requests

Authorization Requests
The following table lists subscriber requests for publications

| Topic Name | Requesting Organization |
|---|---|
| Accutane with no pregnancy test | FDA |
| ADR for Accutane | FDA |
| ADR for Accutane | Centers for Medicare and Medicaid |

→ more authorization requests

Health Topics
Display Topics:
● All topics
○ Containing the word: [          ]  [Display]
                                                → more health topics

Participants
Display Participants:
● All participants
○ Beginning with letters: [          ]  [Display]
                                                → more participants home | contact us | legal | help | log out                              Internet

FIG. 15

Sample view of reporting activity summary on the HCN Portal

Healthcare Collaboration Network
File  Edit  View  Favorites  Tools  Help
Back  Search  Address [                    ] Go  Links  Google  Hotmail  PDC - W3 hcn
Healthcare Collaboration Network

• home
• contact us    • help
• legal          • log out

IBM

Welcome: name  Publisher     Role: Publisher ▼  Change Role

| Publications | Publication Requests | Authorization Requests | Health Topics | HCN Notifications | Participants |

Health Topics
Display Publications:
● All publications
○ Containing the word: [         ] [Display]

| Topic Name | Topic Description |
|---|---|
| Accutane with no pregnancy test | Prescription of Isotretinoin for female with no pregnancy test administered. |
| ADR for Accutane | Prescription of Isotretinoin for a pregnant female. |
| ADR for Arava | A patient prescribed leflunomide (Arava) has elevated levels of AST and bil ... |
| ADR for Arava(2) | A patient prescribed leflunomide (Arava) has elevated levels of AST and bil ... |
| ADR for Clozapine | Agranulocitosis (as measured by neutrophil count) in connection with pres ... |
| ADR for Felbatol | A patient prescribed felbamate (Felbatol) has decreased red blood cell coun ... |
| ADR for Felbatol(2) | A patient prescribed felbamate (Felbatol) has decreased red blood cell coun ... |
| ADR for Felbatol(3) | A patient prescribed felbamate (Felbatol) has decreased red blood cell coun ... |
| ADR for Thalidomide | Prescription of thalidomide (Thalomid) for a pregnant female |
| AMI with ACE Inhibitor | A patient with a diagnosis of Acute Myocardial Infarction received an ACE in ... |

▼ PREV  Page 1 of 49  NEXT ▲
[    ] page  Go

→ return to home page home | contact us | legal | help | log out

Internet

FIG. 17A

Healthcare Collaboration Network
File  Edit  View  Favorites  Tools  Help
◀ Back ▶ ⊗ ☐ ⌂  Search  Address [            ] Go hcn
Healthcare Collaboration Network

• home  • help
• contact us  • log out
• legal
IBM

Welcome: Publisher  [Switch Role to Subscriber]

Publications | Publication Requests | Authorization Requests | Health Topics | HCN Notifications | Participants | Publication Logs

Topic Definition Details

Basic Details
  Topic Name:  AMI Diagnosis - KPJ Demo
  Topic Type:  Quality of Care
  Topic Description:  AMI patients who had Aspirin ordered within 24 hours of admission
  Topic Time Limit:  1 day(s), 0 hour(s)

Topic Trigger Event
  Disease Diagnosis: AMI  [View]

Items of Interest
  Drug Orders:  Aspirin (prescribed)  [View]
  Required matches:  1
  Include in payload:  Matching drug order items only
  Lab Test Orders:

Patient Demographics
  Gender:  Not applicable
  Age:  Not applicable

Include (non-identifying) demographics and procedure orders in message payload: yes → return to home page home | contact us | legal | help | log out                    internet

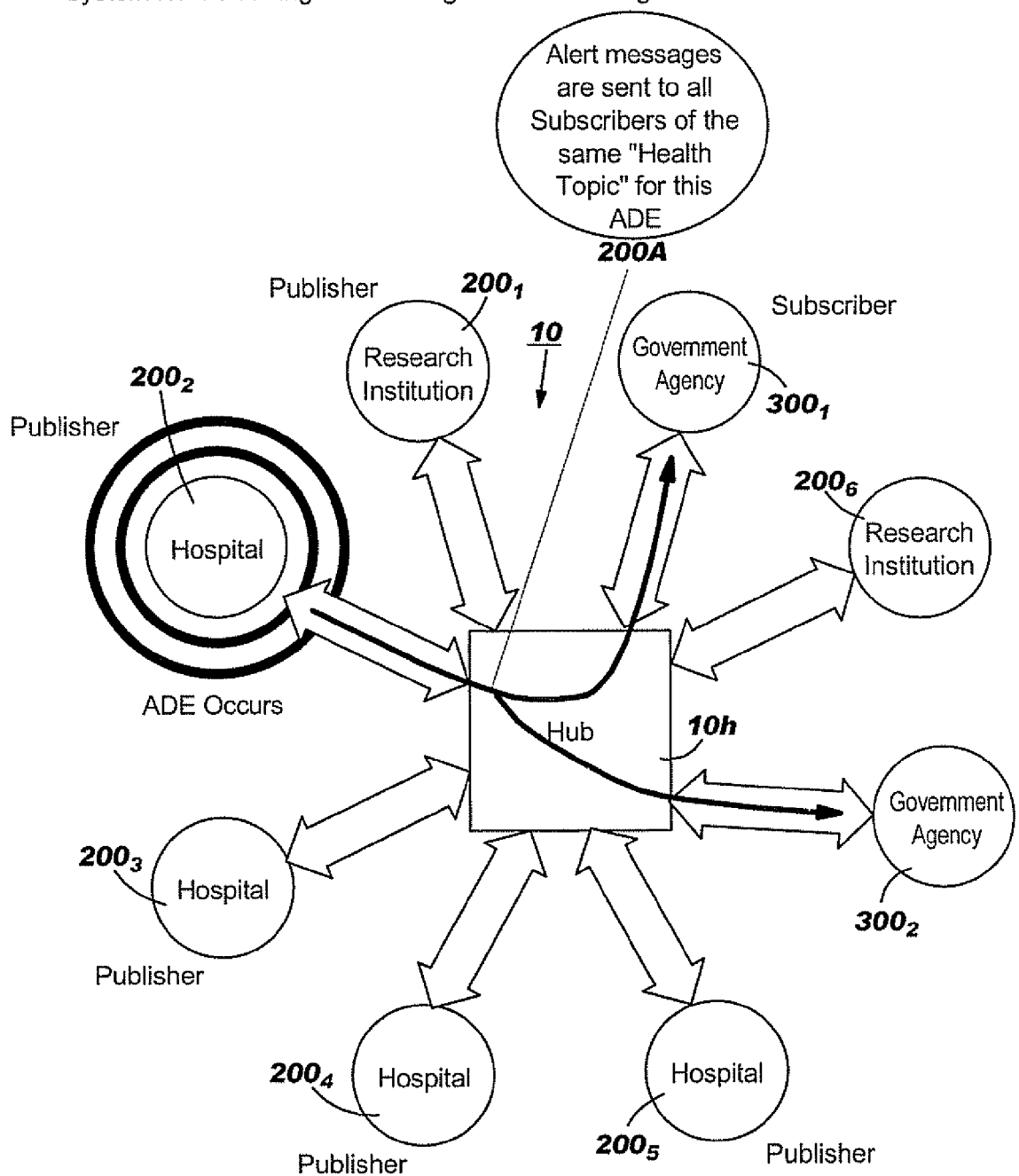

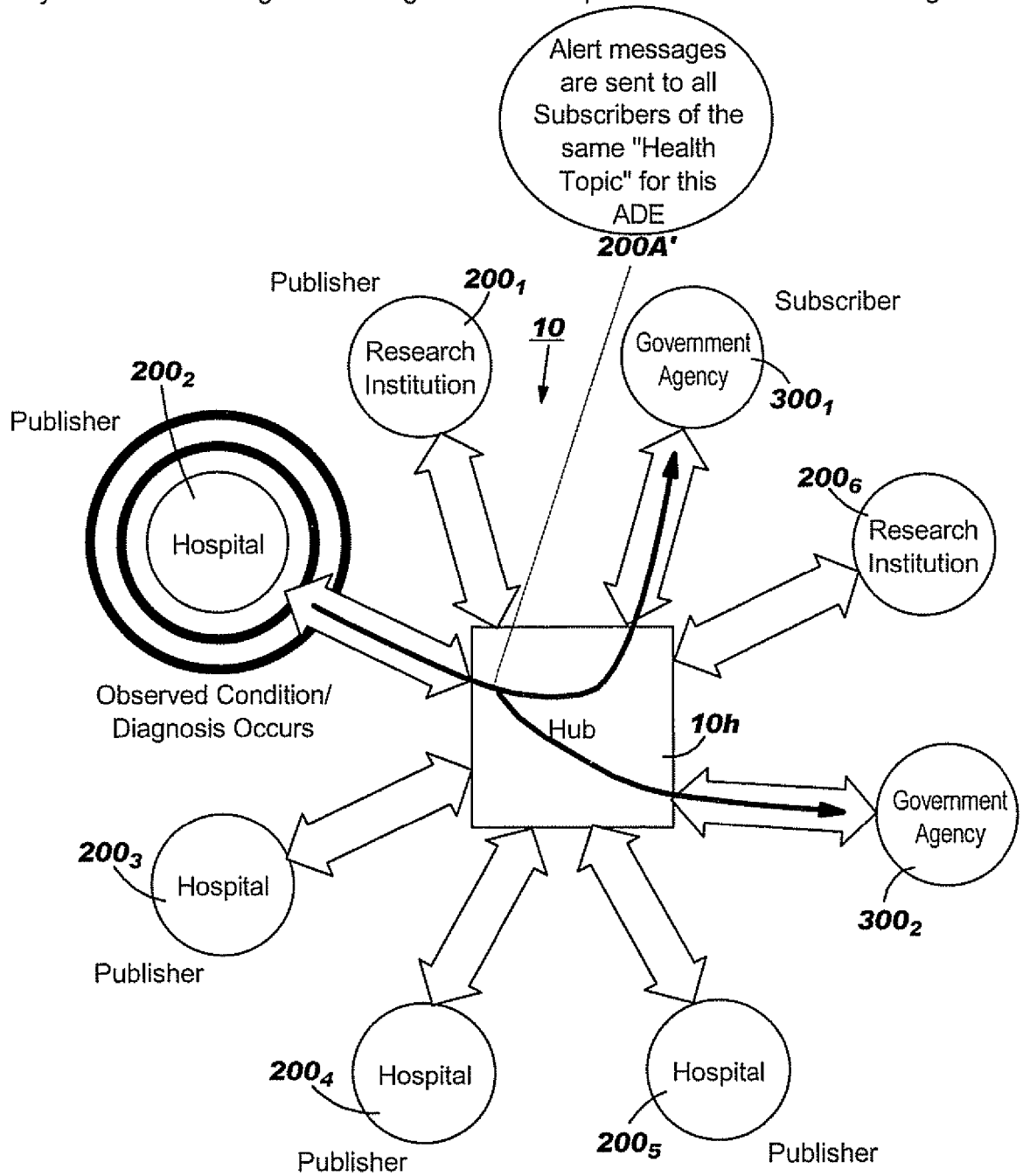

PROVIDING CONTROLLED LEVELS OF COLLABORATIVE EXCHANGE OF DATA FOR REGISTERED PARTICIPATING SUBSCRIBERS AND PUBLISHERS

CROSS-REFERENCE TO RELATED APPLICATIONS

The present application is a continuation of U.S. patent application Ser. No. 11/032,391, now issued as U.S. Pat. No. 7,827,234, entitled "Privacy Entitlement Protocols For Secure Data Exchange, Collection, Monitoring And/Or Alerting," filed on Jan. 10, 2005.

The present application is related to co-pending, co-assigned U.S. patent applications Ser. No. 11/032,590, now issued as U.S. Pat. No. 8,306,831, Ser. No. 11/032,405, now abandoned, Ser. No. 12/147,257, now U.S. Pat. No. 8,364,500, Ser. No. 12/147,276, now U.S. Pat. No. 8,271,294 and Ser. No. 12/147,119, currently pending, and abandoned U.S. patent application Ser. No. 11/032,664.

BACKGROUND OF THE INVENTION

The present invention relates to data sharing using a computer network and may be particularly suitable for healthcare clinical data sharing over an intranet and/or the public Internet.

Healthcare communication systems are typically limited and generally non-standard between institutions and it is difficult to access, track, monitor and/or alert healthcare data across multiple healthcare providers. In the United States, there are over six thousand hospitals, hundreds of thousands of health professionals, and multiple other parties that may desire to exchange clinical data. There are technical, legal and/or societal obstacles for data sharing utilizing centralized data repositories to facilitate the data exchange, and it would be nearly impossible to maintain current awareness and/or access to central data repositories, even if such repositories existed. Further, many privacy organizations oppose a national (or multi-national or global) repository that collects patient information from patients being treated in a healthcare system.

In the past, conventional approaches for exchanging healthcare data included manual transmission of data such as mailing, telephone calls, exchange of data tapes, disks or files in project-specific formats and/or point-to-point interfaces, and/or to use data mining techniques to provide data sharing. That is, some conventional systems have been configured to share diverse data sets and distill information on specific events by Extracting data from the source, Transforming and normalizing the data, then Loading the transformed data into a central repository for data mining ("ETL"). Unfortunately, ETL can make such systems hard to use and may limit the scalability thereof.

BRIEF SUMMARY OF THE INVENTION

Some embodiments are directed to methods for providing entitlement controlled levels of collaborative exchange of data using a computer network of Subscribers and Publishers. The methods include: (a) defining a set of different privacy levels, each privacy level having associated data sharing parameters that control a participating Subscriber's ability to receive content specific data from each Publisher; and (b) providing an electronic privacy level register that identifies for each participating Subscriber what the approved privacy levels are as selected from the set of different privacy levels with respect to each participating Publisher to thereby provide an entitlement based controlled electronic data sharing protocol between Subscribers and Publishers.

Other embodiments are directed to web based healthcare collaborative data sharing systems that include Subscriber and Publisher participants. The Publishers have at least one defined privacy level for different healthcare data content that establishes a data sharing protocol with Subscribers. The Subscribers have at least one defined privacy level that establishes a data sharing protocol with Publishers. The defined privacy levels are selected from a set of common defined privacy levels used by the system for participating Subscribers and Publishers.

Still other embodiments are directed to web-based secure data sharing systems for providing and controlling collaborative healthcare data sharing between Publisher and Subscriber participants using the Internet. The systems include: (a) a Message Flow Server configured to communicate with participant healthcare Publisher Gateways and Subscribers over the Internet; and (b) an Administrative Server in communication with the Message Flow Server. The Administrative Server is configured to control communications between participating Subscribers and Publishers. Each participating Subscriber and Publisher has at least one privacy level selected from a defined set of privacy levels. The Administrative Server is in communication with an electronic privacy level register that defines a privacy level for certain types of patient healthcare data. The system is configured to control the communication between Subscribers and Publishers based on respective privacy levels thereof.

Other embodiments are directed to healthcare collaborative data sharing computer network systems that include: (a) a Message Flow Server; (b) a plurality of Publisher participants having access to electronic patient healthcare records in communication with the Message Flow Server; and (c) a plurality of Subscriber participants in communication with the Message Flow Server. Each Publisher includes at least one Publisher Gateway. The Publisher Gateway is configured with at least one defined privacy level that electronically controls its data sharing protocols for receiving and relaying electronic communications from and to the respective Subscribers. Each Subscriber has a defined privacy level that controls their access to healthcare data from the participating Publishers. Healthcare data related to a healthcare topic is selectively electronically automatically forwarded to a Subscriber from a Publisher Gateway by the Message Flow Server only if a Subscriber has a privacy level that entitles the Subscriber to healthcare data for that topic.

Still other embodiments are directed to computer program products for controlling data sharing in a collaborative data sharing system using a computer network. The computer program product includes a computer readable storage medium having computer readable program code embodied in the medium. The computer-readable program code includes: (a) computer readable program code configured to define at least one privacy level for each Publisher and Subscriber, the at least one privacy level being selected from a global set of defined privacy levels, the different privacy levels associated with different contents of data records; (b) computer readable program code configured to define data sharing protocols for Subscribers requesting data and Publishers having data based on the defined privacy levels; and (c) computer readable program code configured to provide a participant registry of Subscribers and Publishers and defined privacy levels thereof.

It is noted that embodiments and/or features described with respect to a particular type of implementation can be implemented in other ways, such as, for example, where embodiments are described as methods those features can be implemented as computer program products and/or devices or systems. These and other objects and/or aspects of the present invention are explained in detail in the specification set forth below.

BRIEF DESCRIPTION OF THE SEVERAL VIEWS OF THE DRAWINGS

FIG. 1D is a schematic illustration of the system shown in FIG. 1A illustrating that data can be input to a Publisher Gateway at an originating source Publisher and that publications (in different output formats) can be transmitted back to entities within or associated with the originating Publisher according to embodiments of the present invention.

FIG. 2 is a flow chart of exemplary operations that can be used to carry out certain embodiments of the present invention.

FIG. 13 is a sample message that includes diverse data records for a patient according to embodiments of the present invention.

FIG. 14 is a screen printout of an exemplary computer network (typically the web) portal for a Publisher according to embodiments of the present invention.

FIG. 15 is a screen printout of an exemplary topic catalog listing accessible on a computer network portal according to embodiments of the present invention.

FIGS. 17A-17C are screen views that can be used to interact with the system regarding publication of a topic(s) of interest according to embodiments of the present invention.

FIG. 18 is a schematic illustration of a healthcare system used to identify and generate an Adverse Drug Event alert according to embodiments of the present invention.

FIG. 19 is a schematic illustration of a healthcare system used to identify and generate an alert identifying of a disease outbreak, a public health risk, an environmental hazard and/or bioterrorism event according to embodiments of the present invention.

DETAILED DESCRIPTION OF THE INVENTION

Figure 1A:
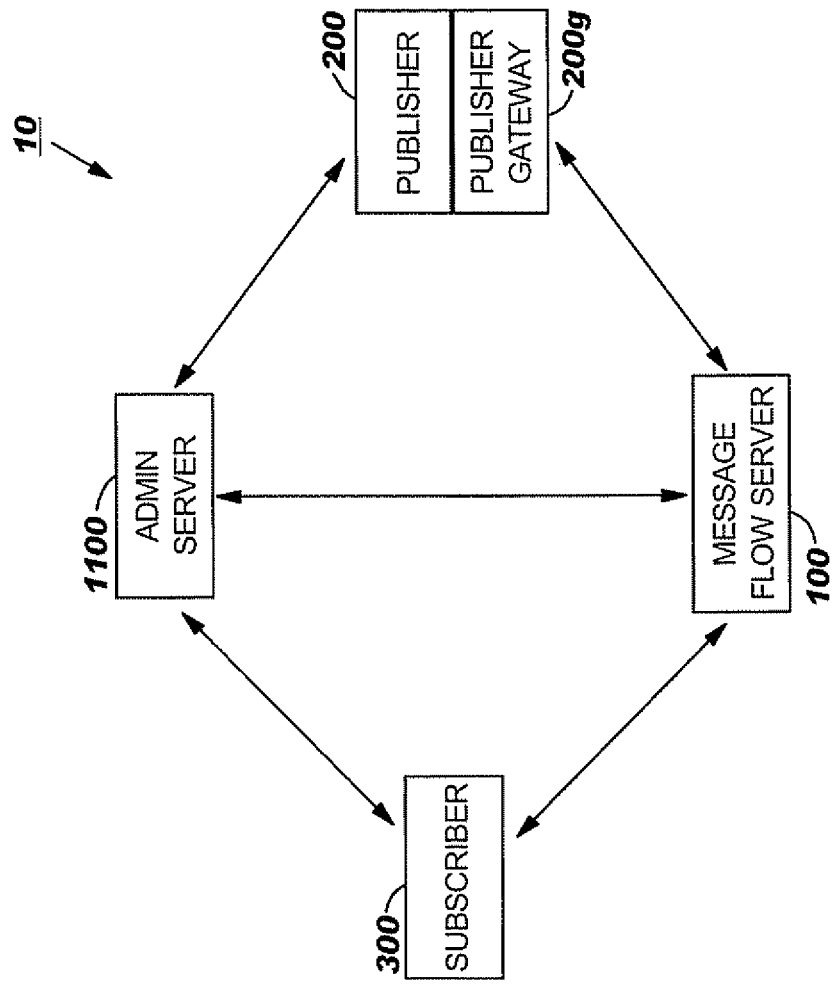
FIG. 1A is a schematic illustration of a computer networked system used to provide collaborative data exchange according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the claims or figures unless specifically indicated otherwise. Where used, the terms "attached", "connected", "contacting", "coupling" and the like, can mean either directly or indirectly, unless stated otherwise.

As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "Publisher" means a participant that can provide or "publish" data to an external and/or internal site using a computer network. The Publisher is typically an original data source. The term "Subscriber" means a participant that can request topical data using a computer network. Publishers can be Subscribers to their own data or to other participating Publisher's data. The term "automatic" means that substantially all or all of the operations so described can be carried out without the assistance and/or manual input of a human operator. The term "electronic" means that the system, operation or device can communicate using any suitable electronic media and typically employs programmatically controlling the communication between participants using a computer network. The term "hub" means a node and/or control site (or sites) that controls data exchange between Publishers and Subscribers using a computer network. The hub may not be required for a Publisher site to access its own messages (i.e., where the healthcare data request is from a Subscriber within the Publisher institution and is only for institution specific data, typically controlled by the Publisher Gateway, from the Publisher institution). The term "HIPAA" refers to the United States laws defined by the Health Insurance Portability and Accountability Act. The term "open standard(s)" refers to standardized electronic formats of data using standards that are open to the public (i.e., non-proprietary). Examples of current open-standard messaging formats include HL-7, MAGE-ML, and relevant industry standard codes presently existing or yet to be developed. For example, for healthcare applications, industry standard codes can include, but are not limited to those used for diagnosis (ICD-9, ICD-10), procedures (CPT), lab results (LOINC and/or SNOMED) and drugs (NDC, RxNorm).

The term "message" means one or more data elements for a topic that can be in a defined computer code language format. There can be different message types, such as, but not limited to, command and control messages, clinical or target data publication messages, notification messages, and alert messages. The messages can include elements received from Publisher-specific internal IT computer systems, typically HL7 message formats. The publication of target data can be carried out as a topic publication message that can be transmitted to a Subscriber by way of their respective gateways. The topic publication message can include a content definition header, which can be in a different format from other data elements in the topic publication message (such as in XML). Typically, the data to be transmitted with the header is enclosed in the body of the message (called an envelope or enclosure), and what resides in the envelope can generally be data in any arbitrary industry specific format. The other data elements in the topic publication message can be in industry specific format and/or code or mapped to a defined standardized message code/content for a defined communication protocol/common language between all participants. For example, for healthcare data sharing systems, the topic publication message can include a content definition summary/header and include those clinical data elements associated with a Subscriber's data request. The message data elements can be configured to generate a (typically short) text summary of that data element.

Embodiments of the present invention may be particularly suitable for collaborative healthcare data sharing systems that one or more can be implemented using a computer network. The term "computer network" includes one or more local area networks (LAN), wide area networks (WAN) and may, in certain embodiments, include a private intranet and/or the public Internet (also known as the World Wide Web or "the web"). The healthcare or other data sharing systems contemplated by embodiments of the present invention may be implemented as one or more of a state system, a regional system, a national system and/or a multi-national system.

The terms "healthcare data" and "clinical data" are used interchangeably and include any and/or all of a treatment, medicinal, drug or prescription use, laboratory tests and/or results, diagnostic information, demographic information, a physical location, a home address (such as a zip code) or travel or other relevant data associated with an event or patient. The healthcare data can be used for clinical trials, adverse drug events, disease surveillance (such as for infection containment or alert) or other bio-surveillance and/or quality of care evaluations. Embodiments of the present invention can also be used for non-healthcare systems. The non-healthcare systems can be configured to provide systems for application-specific data. Thus, for clarity of discussion, the present invention will be primarily discussed herein with respect to healthcare systems, but the features, components and/or operations are not limited thereto.

It is also noted that embodiments of the invention may be discussed with respect to IBM specific products for completeness of discussion. However, the invention is not limited thereto as other products and/or suppliers may be used to implement the invention.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). As will be discussed further below, typically, some program code executes on each Publisher Gateway computer and some program code executes on a hub server (such as a Message Flow Server and/or a web application or Administrative Server) with communication between the gateways and the hub server using the Internet.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Embodiments of the present invention will now be discussed with respect to the figures. FIG. 1A illustrates an exemplary electronic collaborative data sharing system 10 that includes a Message Flow Server 100 in communication with an Administrative Server 1100. As shown, the system also includes participant Publishers 200 and Subscribers 300 (shown as one of each for ease of discussion). The Administrative Server 1100 can be configured to control participant access and communicate with the Message Flow Server 100 so that only Publisher-approved publications are transmitted or routed to Subscribers responsive to Publisher input. The function of all or some of the Administrative Server 1100 can be incorporated into the Message Flow Server 100. Typically, however, the Administrative Server 1100 is separate from the Message Flow Server 100 and communicates electronically therewith. Similarly, although shown as two servers, more than two servers can be used to carry out either the Message Flow Server 100 or Administrative Server 1100 functions. It will be appreciated by those skilled in the art that the functions may be combined in a single physical node.

Each Publisher 200 can include at least one Publisher Gateway 200g. The Publisher Gateway 200g communicates with the Message Flow Server 100 to transmit (their internally authorized) publication data to Subscribers 300. The Publisher 200 typically includes a private intranet of affiliated departments (such as admission and/or discharge), physicians, laboratories, and pharmacies as will be discussed further below. The gateway 200g is configured to collect clinical data from a respective Publisher 200. In some embodiments, the gateway 200g is configured to collect only temporal data, based on the size of the storage media.

The Subscriber 300 can receive approved clinical publication data from participating Publishers 200 by any suitable communication means, including one or more of wireless messaging to PDA's, wireless communication systems (such as cellular telephones), personal or business computers, portable computers, via email (with or without attachments), voicemail, storage into a database or storage medium associated with the Subscriber, a Subscriber Gateway (300g, FIG. 6) and the like. The publication data can be provided as a clinical topic publication message in a format that a Subscriber 300 can select. The Subscriber 300 can request different publication formats or destinations for different publication data. The destination may be established during site installation or configuration or may be effectuated by the Administrative Server 1100 at start-up or in response to a change request. In some embodiments, the conditions or rules for publication, subscription, destination and data format can be controlled/established using the Administrative Server 1100.

Figure 1B:
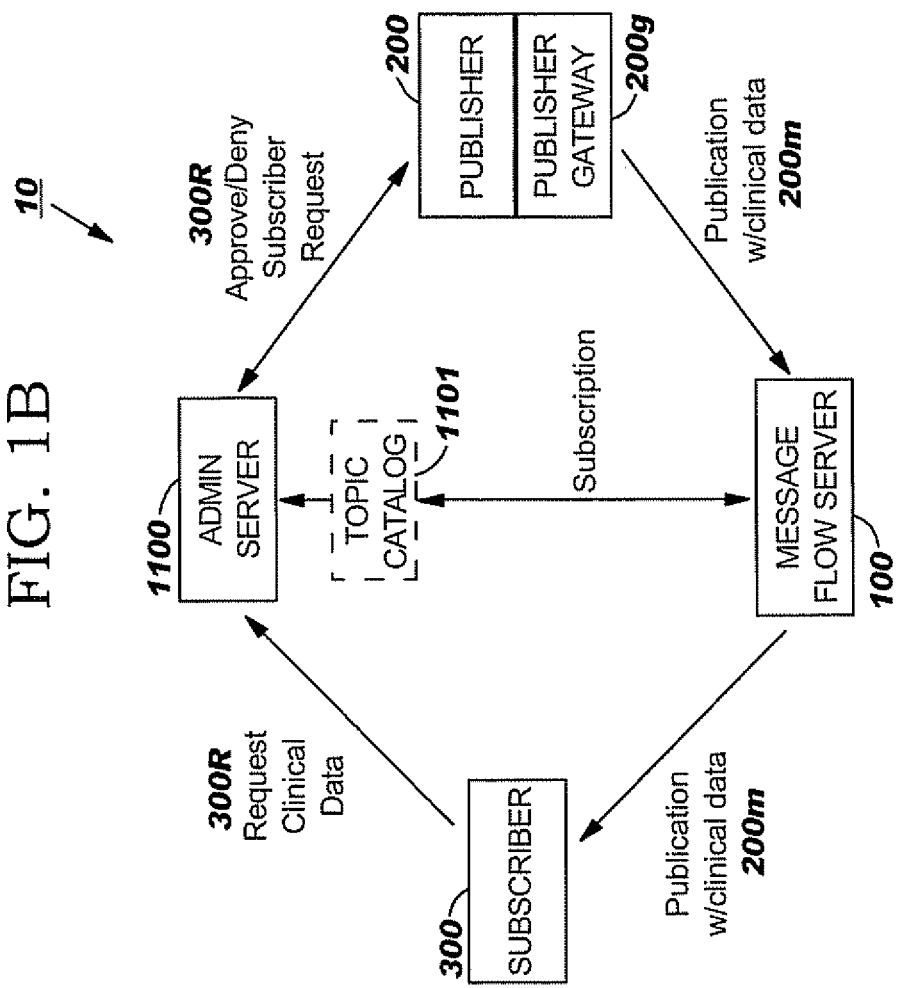
FIG. 1B is a schematic illustration of the system shown in FIG. 1A illustrating an exemplary publication cycle according to embodiments of the present invention.

As shown in FIG. 1B, the system 10 can include a topic catalog of different data types or content, that may have different publication rules, that may be of interest. The electronic topic catalog 1101 can be a global topic catalog 1101 that is displayed by the Administrative Server 1100 to the Subscribers and Publishers 300, 200. A Subscriber 300 can select a topic of interest from the topic catalog 1101 or create a new topic if the existing topics do not have the desired content, format, and/or security level. The desired message format may be requested by creating or selecting a topic with a content-constraint that selects the desired format. That is, within the topic catalog, two different topics may have the same data content but be different topic entries in the topic catalog based on the desired output format and/or communication mode, dictating how the requested data is transmitted to them.

Still referring to FIG. 1B, an exemplary publication cycle is shown. A Subscriber 300 accesses the system at a portal hosted by the Administrative Server 1100 and enters a request for clinical data 300R. The Administrative Server 1100 can forward a Subscriber request for publication 300R to a Publisher 200 using the system portal (Administrative Server Web Application). Typically, the request is approved or denied upon review by a person (rather than electronically) by each respective Publisher 200. The request for a particular Subscriber and topic may be approved once. Typically, the Administrative Server 1100 sends a request notification and the Publisher responds to the request notification using the Administrative Server web application. Hence, in operation, the request notification message and request response (as well as the Subscriber notification regarding same) can electronically travel to and from Subscribers/Publishers through the Administrative Server.

In some particular embodiments, one or more Publishers 200 can be configured with electronic filters or constraints that can automatically electronically approve or deny the publication requests for some or all of the topics. In addition, in some embodiments, a Publisher 200 can pre-identify to the Administrative Server 1100 those Subscribers that they have a standing "deny" for (whether by topic or identity of the Subscriber). In such a situation, the Administrative Server 1100 can be configured to not send Requests for publication from the identified "blacklist" Subscriber and/or "topic".

Once a Publisher 200 approves a publication request 300R for a particular Subscriber 300, any ongoing clinical data collected or aggregated for a patient in their gateway that meets that topic (content definition) request 300R can be published to the Message Flow Server 100 as a publication 200*m* which is then automatically forwarded to the requesting and approved Subscriber 300. This can be described as a Publisher-specific approved subscription for a particular topic with defined data content to a particular Subscriber. For a particular Publisher publication transmitted by a respective Publisher 200, there can be many approved Subscribers having approved subscriptions. When a Publisher 200 transmits a publication with topical data 200*m* to the Message Flow Server 100, it can be "broadcast" to multiple approved Subscribers 300 generally concurrently. To cancel a subscription, a respective Publisher 200 can access the system portal of the Administrative Server 1100 and transmit a subscription cancellation order for one or more Subscribers and/or for a particular topic. This will prevent future publication transmissions (for a selected topic or topics or all topics) from that Publisher 200 from being sent automatically to that Subscriber 300.

Figure 1C:
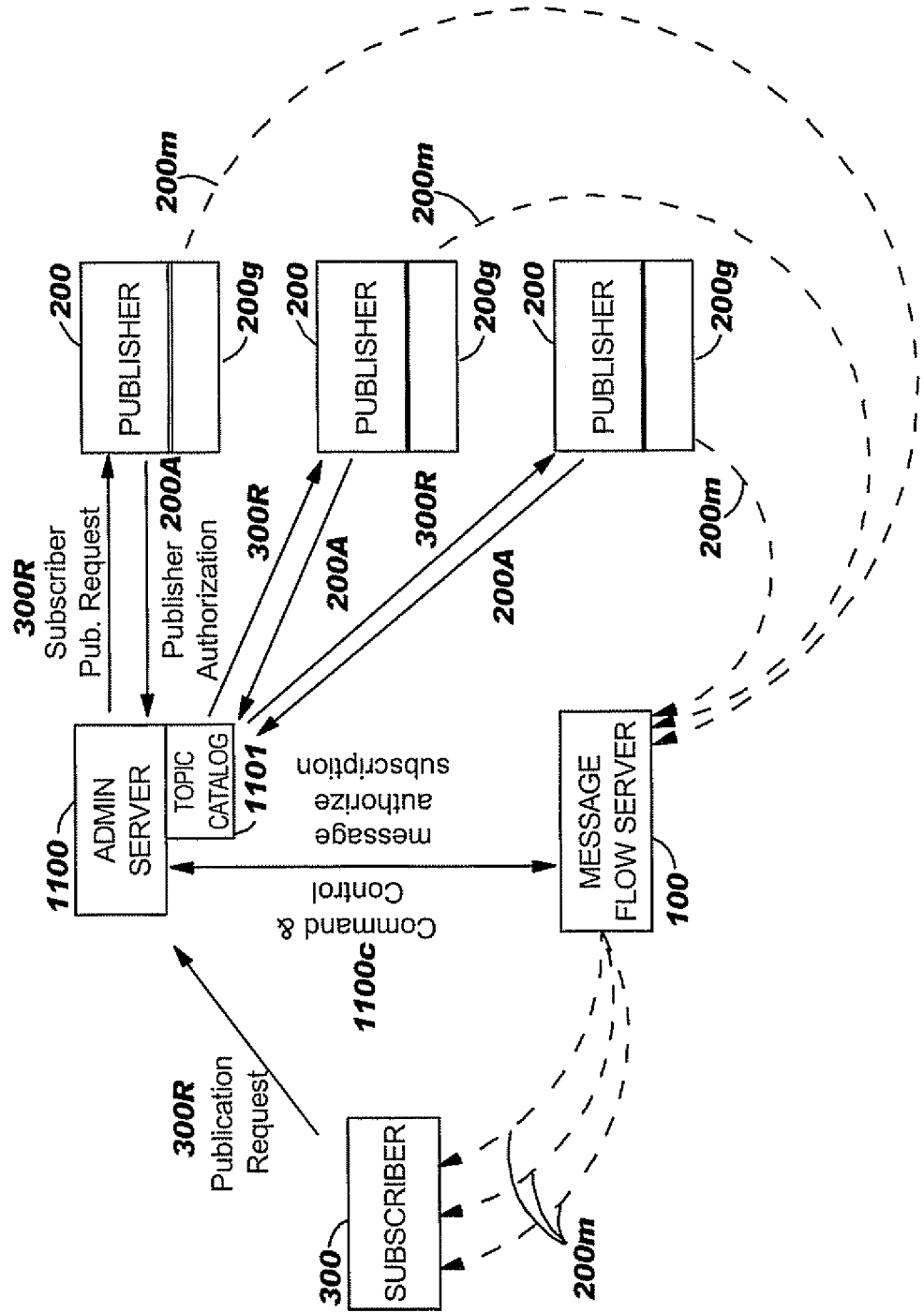
FIG. 1C is a schematic illustration of the system shown in FIG. 1A illustrating an exemplary publication cycle of a selected Subscriber topic and between a Subscriber and a plurality of different Publishers according to embodiments of the present invention.

FIG. 1C illustrates that the communications between the participants and servers, 1100, 100 can be message-based communications. As shown, the Subscriber 300 can select (or create) a request for publication of a particular topic 300R from the topic catalog 1101. This generates a notification of a publication topic request 300R that the Administrative Server 1101 can display on the Publisher screen of the system portal. The publication topic request 300R will define a topic title or name (which has an associated topic description) for the relevant clinical data of interest and identify the requesting Subscriber. The Publisher 200 responds to request for publication by approving or denying the request and sending a message to the Administrative Server 1100. As shown, each Publisher 200 sends an approval response 200*a* to the Administrative Server 1100. If approved, the Administrative Server 1100 sends a command and control message 1100*c* to the Message Flow Server 100 to notify the Message Flow Server 100 that a Subscriber 300 has an approved subscription and is entitled to receive publication messages 200*m* sent from a particular Publisher for that approved topic. As shown, for a single publication topic request from a Subscriber 300, the Message Flow Server 100 can receive and transmit many topic publication messages of clinical data 200*m* from different Publishers 200.

Figure 7:
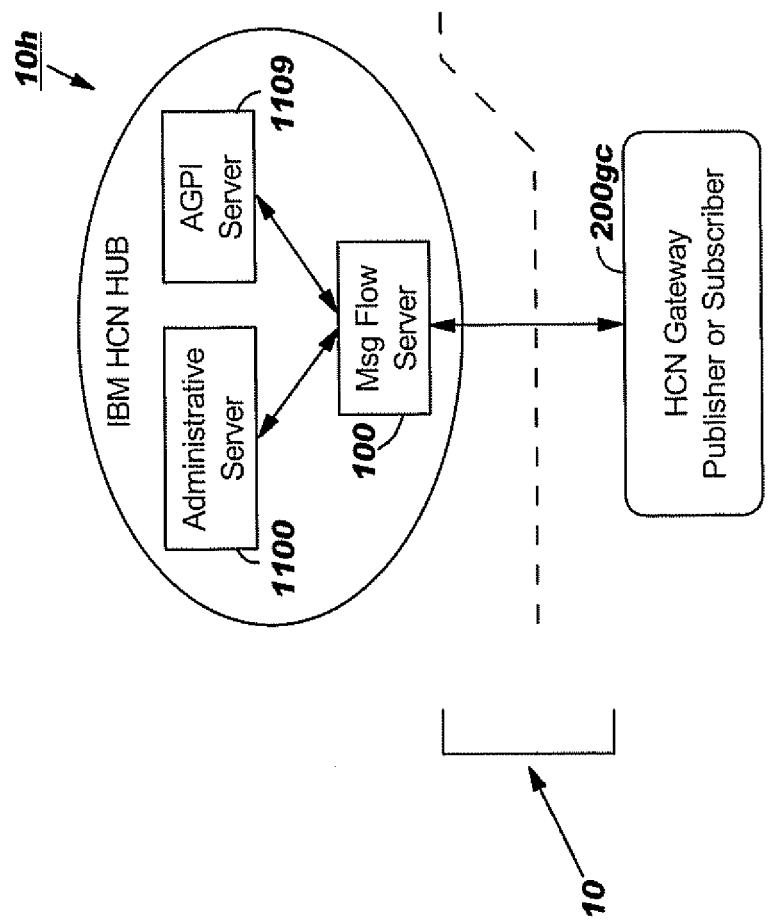
FIG. 7 is a schematic illustration of components of a hub according to embodiments of the present invention.

One or more of the Publisher Gateways 200*g* can also be configured as a Subscriber Gateway 300*g* to be a common gateway 200*gc* for both functions to thereby accept external data as a Subscriber and to transmit internal data as a Publisher as shown in FIG. 7. In other embodiments, a Subscriber 300 can communicate without the use of a Subscriber Gateway 300*g* as noted above, or a Subscriber 300 can have a dedicated Subscriber Gateway 300*g*.

Figure 6:
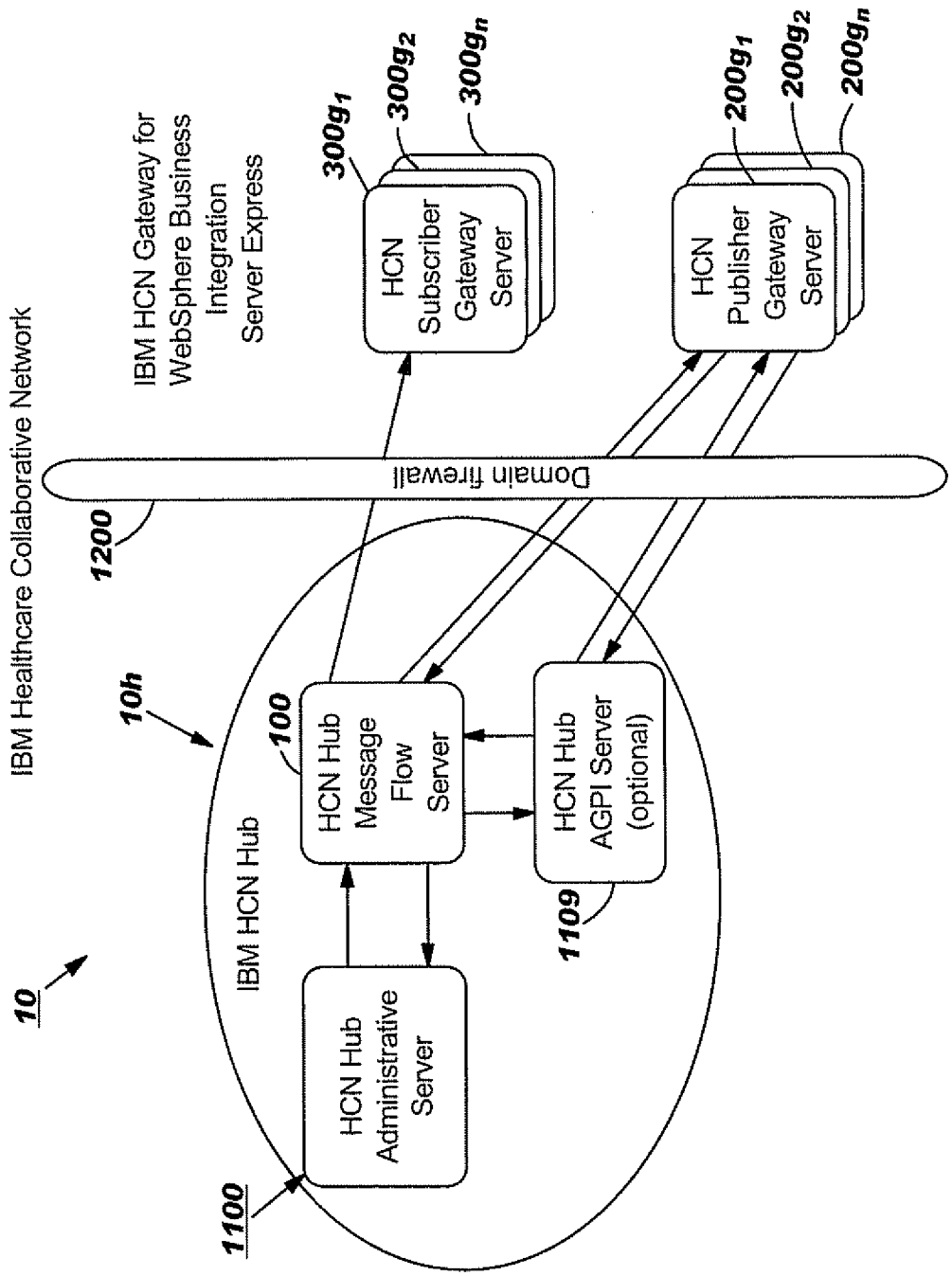
FIG. 6 is a schematic illustration of a collaborative computer network system according to embodiments of the present invention.

FIG. 1D illustrates that some Subscribers 300 can be affiliated with the Publisher 200. The Message Flow Server 100 can transmit or route selected clinical data to the Subscribers 300 within the Publisher's organization (as well as to external Subscribers). The Message Flow Server 100 can communicate with the Subscribers 300 through the Publisher Gateway 200*g*, with the Publisher Gateway 200*g* configured to have dual modality operation/function to thereby also act as a Subscriber Gateway 300*g* thereby utilizing a common Subscriber/Publisher Gateway 200*gc* (FIG. 7) or through a separate Subscriber Gateway 300*g* (FIG. 6). In other embodiments, the Message Flow Server 100 can transmit the clinical data and/or requested information directly to the Subscribers 300 using their elected electronic communication modality as discussed above. The Subscribers 300 can include administrators, physicians, department heads, or other functions or persons desiring clinical data. As noted before, the clinical data can be transmitted to the Subscriber in one or more formats, including, but not limited to, email, download or transmission to a database or electronic storage medium, pages, text or voice messaging via telephone or wireless communication devices including cellular phones and PDA's or other portable and/or pervasive computing devices. For example, a clinician can subscribe to receive clinical data from their own healthcare institution that notifies him or her of cardio patients (or other healthcare department or specialty) exhibiting certain symptoms or selected criteria such as a prescribed medication.

This information can be sent in any suitable format, such as to a portable communications device to allow for more prompt notification and allow for any care follow-up as desired. In another example, an administrator can request clinical data for all patients having a hospital stay that is over a defined threshold for various diagnosis or other criteria for healthcare standard of care monitoring reports. In yet another example, the department head may subscribe to a topic for publication messages from his or her respective care facility that includes, for example, notification of patients treated by physicians within his or her department that were prescribed a certain medication or not prescribed a certain medication for particular symptoms, lab work and/or diagnosis. This may identify training needs or patient follow-up.

The system 10 can include large numbers of participant Subscribers and Publishers. Although shown in the figures as a single Message Flow Server 100, at a single node, a plurality of such servers and/or nodes may be used as appropriate for redundancy and/or service.

For healthcare applications, one class of Publishers of data are typically care providers such as hospitals, clinics, nursing homes, rehabilitation centers, urgent care facilities, laboratories, physicians and other care providers, particularly those providers that are under an obligation to report clinical data to regulatory agencies. Other classes of Publishers can include independent laboratories, pharmacy benefit managers, and other clinical repositories.

Typical Subscribers include federal, state and/or local (local to a Publisher site) regulatory and/or governmental agencies, any public health agency, clinics or hospitals (which may also be Publishers), insurers, pharmaceutical companies, researchers, public health and/or policy institutions/agencies, and the like. The system 10 can be used as part of a National Health Information Infrastructure (NHII) and/or Regional or State Health Information Organization (s).

In some embodiments, a third category of participant, which may be described as an observer, may optionally be present. An observer may have standard monitoring protocols established, by which the observer can obtain copies of clinical data, data messages and/or summaries of messages sent to and/or from certain or all Publishers 200 and/or certain and/or all Subscribers 300. In addition, there may be a fourth administrative category participant for the hosting service (not shown).

For Internet based applications, the Message Flow Server 100, Subscribers 300, Publishers 200 and/or associated gateways 200*g*, 300*g* can be configured to operate using SSL (Secure Sockets Layers) and a high level of encryption. The users or participants can be assigned to "organizations" which have a set of attributes that process data for their systems. The system 10 has a registry of user's that define the user's role and provide a specific level of authority, which is identified at the web portal (such as upon sign on). The Publishers 200 and Subscribers 300 communicate with the hub 10*h* via the web portal 10*p* (FIGS. 6, 8) and Administrative Server 1101 to publish clinical data from one or more Publishers 200 on topics to interested Subscribers 300 via the Message Flow Server 100 that is controlled by the Administrative Server 1100.

FIG. 2 illustrates operations that can facilitate collaborative sharing of data using an Administrative Server 1100 and a Message Flow Server 100 according to embodiments of the present invention. As shown, a request to publish a selected topic is received by the Administrative Server (block 105). The Administrative Server can assess whether the Subscriber is authorized to receive data from participating Publishers (such as from any, all or only selected Publishers) (block 110). The publication request can be forwarded to Publishers so that each Publisher can approve or deny the publication request for a particular topic or Subscriber (block 115). In particular embodiments, the Subscriber topic request may be pre-screened by the Administrative Server to see if any "blacklist" or standing instruction exists from a particular Publisher for a particular Subscriber or topic. If a Publisher approves the publication request for a particular topic from a particular Subscriber an authorized standing subscription order can be established, allowing clinical data to be automatically sent from the approving Publisher to the authorized requesting Subscriber via the Message Flow Server 100 (block 116). The Administrative Server 1100 can transmit a subscription message to the Message Flow Server to initiate the subscription and allow clinical data to be routed from the Publisher to the Subscriber via the Message Flow Server without requiring the requestor to request publication for future events or data on that topic from that Subscriber.

Figure 3:
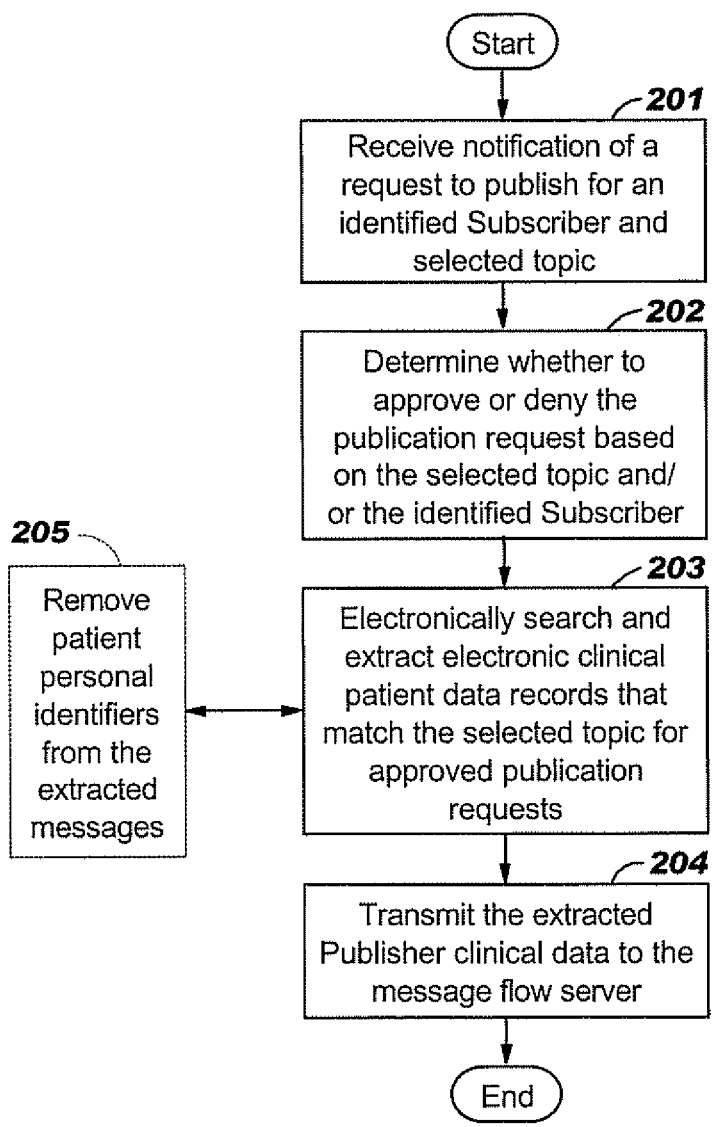
FIG. 3 is a flow chart of other exemplary operations that can be used to carry out embodiments of the present invention.

FIG. 3 illustrates exemplary operations that can be carried out by a Publisher 200. As shown, a notification of a request to publish is received at the Publisher portal (the Administrative Server application) for an identified Subscriber and topic (block 201). The notification can be on any viewing screen, but is typically in the "inbox" of the Publishers. The Publishers can each determine whether to approve or deny the publication request for a respective Subscriber and/or topic request. The Publishers can review the notification and respond to the web application portal an approval or denial based on Publisher specific preferences, criteria, rules and/or constraints (block 202). The Publisher approval and/or denial for the request can be selected on the web application portal and sent as a notification from the Administrative Server to the Subscriber. The notification may be viewed by the requesting Subscriber in an "inbox" of the Subscriber portal.

The Publisher Gateway can be in communication with a message queue database of electronic patient data records that have been aggregated and configured into standardized message data formats, typically open-standard message formats, to form electronic clinical data message records of patients. The Publisher Gateway can electronically search and extract messages of patient record data that match the selected topic for approved publication requests (block 203). The extracted Publisher patient data messages can be transmitted to the Message Flow Server (block 204). In some embodiments, the patient data messages can be filtered to automatically and/or electronically to remove certain information, such as personal identifiers, prior to the transmission (block 205). The optional filtering can be used based on the rules of the Publisher (to comply with business or regulatory rules, such as HIPAA privacy rules or the like), or can be based on the identity of the Subscriber requesting the data and/or on the topic requested for publication.

The message queue database can be configured to include a finite time period of patient data messages, typically between about 30-120 days, and more typically about 30 days, depending on the size of the storage media. The older message data maybe purged or transferred to one or more Publisher controlled history databases for subsequent use, such as for historical trend analysis as desired. In the periodically purging embodiment (typically a first-in, first-out (FIFO) based purging protocol), the system 10 acts as a temporal system that can provide relatively current clinical data. The Publishers 200 can be configured to cache data so that data that is older or unused (not marked as received recently, "in-use" or used recently, such as within the last 30-60 days) can automatically electronically "fall-off" the end of the cache time period (the cache period being typically limited by hardware storage limitations). The Subscribers 300 can have repositories that store or cache the messages into their own historical databases or systems. Thus, in some embodiments, there is no central repository of patient data. The Publisher Gateway 200*g* may also have other circuits or modules, such as a message cache that can suspend transmission of the extracted patient data message(s) pending receipt of additional patient data (aggregation of different inputs from labs, pharmacies, and the like) for a more complete response to a topic as will be discussed further below.

The publication request from a Subscriber can be in the same standardized message format as the published patient data messages from the Publishers (e.g., HL7). The publication of Publisher data messages can be an event-based operation whereby a publication can be generated in substantially real-time from when a patient record is identified as meeting the data content of an approved subscription topic to a Subscriber request for publication (typically in less than an hour, and in some embodiments in less than about 10 minutes). In other embodiments, the evaluation of data records may be performed at desired intervals on defined or in situ applied evaluation cycles.

Figure 4:
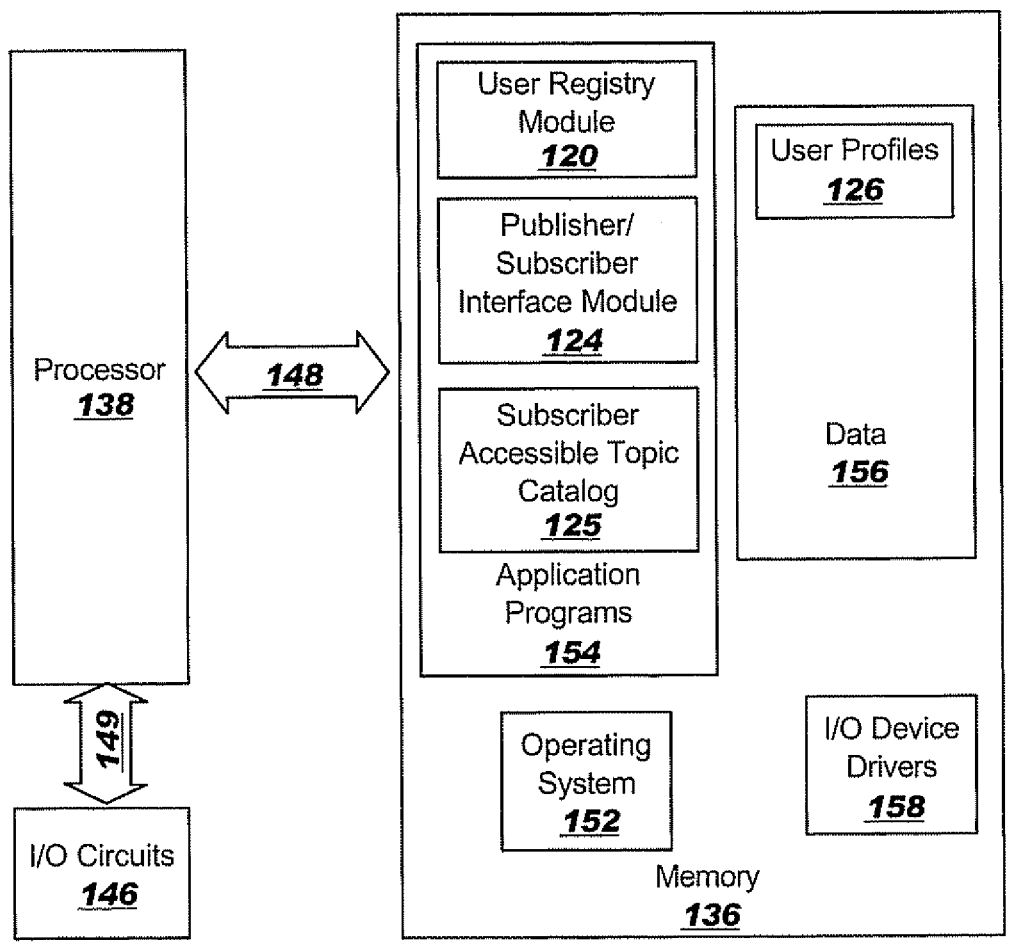
FIG. 4 is a block diagram of a data processing system according to embodiments of the present invention.
Figure 5:
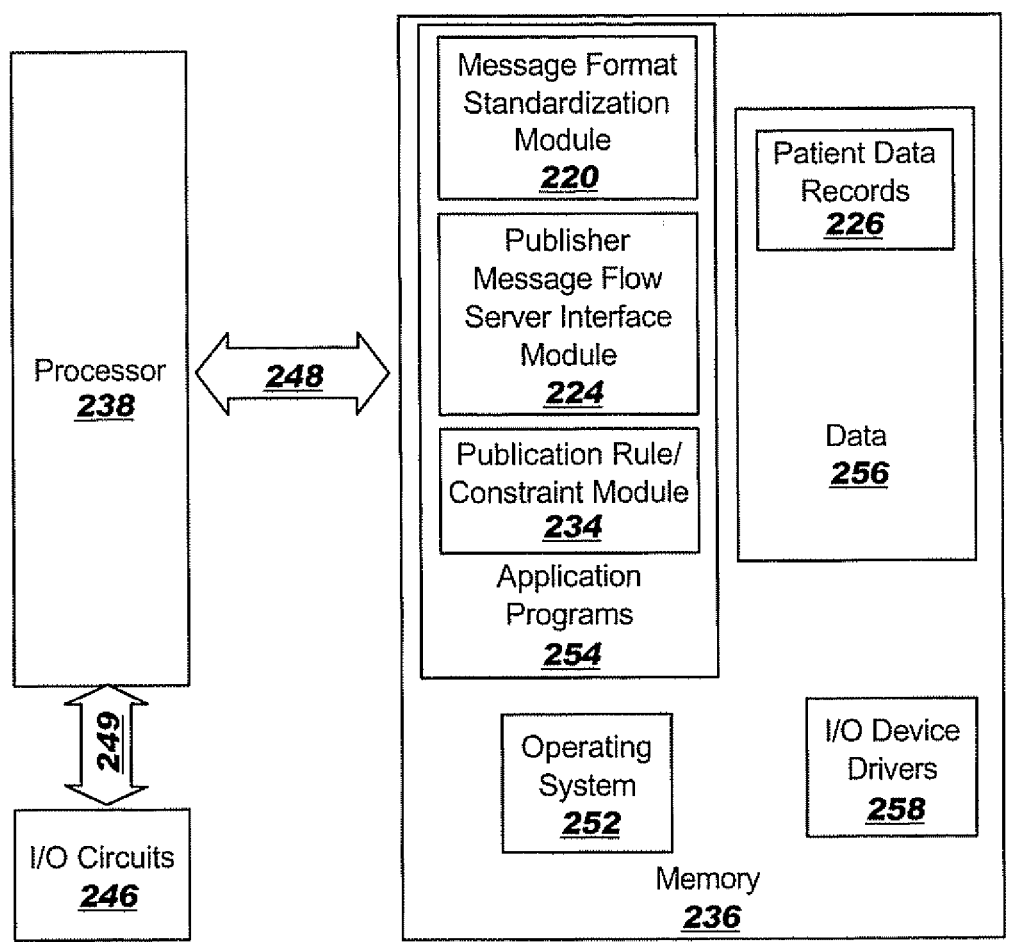
FIG. 5 is a block diagram of a data processing system according to embodiments of the present invention.

FIGS. 4 and 5 illustrate exemplary data processing systems or database environment that may be included in devices operating in accordance with some embodiments of the present invention. As illustrated in FIG. 4, a data processing system which can be used to carry out or direct operations of the hub and/or web application (Administrative Server) and/or Message Flow Server, includes a processor 138, a memory 136 and input/output circuits 146. The data processing system may be incorporated in, for example, one or more of a personal computer, server, router or the like. The processor 138 communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

Similarly, FIG. 5 illustrates a data processing system, which can be used to carry out and/or direct operations of the Publisher Gateway, includes a processor 238, a memory 236 and input/output circuits 246. The data processing system may be incorporated in, for example, one or more of a personal computer, server, router or the like. The processor 238 communicates with the memory 236 via an address/data bus 248 and communicates with the input/output circuits 246 via an address/data bus 249. The input/output circuits 246 can be used to transfer information between the memory (memory and/or storage media) 236 and another computer system or a network using, for example, an Internet protocol (IP) connection. These components may be conventional components such as those used in many conventional data processing systems, which may be configured to operate as described herein.

In particular, the processor 138, 238 can be commercially available or custom microprocessor, microcontroller, digital signal processor or the like. The memory 136, 236 may include any memory devices and/or storage media containing the software and data used to implement the functionality circuits or modules used in accordance with embodiments of the present invention. The memory 136, 236 can include, but is not limited to, the following types of devices: cache, ROM, PROM, EPROM, EEPROM, flash memory, SRAM, DRAM and magnetic disk. In some embodiments of the present invention, the memory 136, 236 may be a content addressable memory (CAM).

As further illustrated in FIGS. 4 and 5, the memory (and/or storage media) 136, 236 may include several categories of software and data used in the data processing system: an operating system 152, 252; application programs 154, 254; input/output device drivers 158, 258; and data 156, 256. As will be appreciated by those of skill in the art, the operating system 152, 252 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158, 258 typically include software routines accessed through the operating system 152, 252 by the application programs 154, 254 to communicate with devices such as the input/output circuits 146, 246 and certain memory 136, 236 components. The application programs 154, 254 are illustrative of the programs that implement the various features of the circuits and modules according to some embodiments of the present invention. Finally, the data 156, 256 represents the static and dynamic data used by the application programs 154, 254 the operating system 152, 252 the input/output device drivers 158, 258 and other software programs that may reside in the memory 136, 236.

With respect to FIG. 4, the data 156 may include participant or user profile type data 126 that defines a Publisher willingness to receive requests of publication of data from different Subscribers or topics for use by the circuits and modules of the application programs 154 according to some embodiments of the present invention as discussed further herein. For example, affiliated Subscriber hospitals or clinics may have a higher level of entitlement to receive records from each related or affiliated Publisher relative to non-affiliated entities. In other examples, non-affiliated but approved Subscribers (such as governmental agencies) may also have high-levels of entitlement.

With respect to FIG. 5, the data 256 may include electronic patient data records 226. The patient data records can comprise patient data records that have been mapped and parsed into patient data messages for use by the circuits and modules of the application programs 254 according to some embodiments of the present invention as discussed further herein. In some embodiments the patient data records held by a Publisher can include, for example, first name, last name, social security number, opaque identifier (used to provide patient-specific privacy while providing traceability to the source Publisher and indirect traceability to the patient), gender, birth date, address, telephone number, birth place, blood type, age, height, weight, eye color, hair color, race and/or gene signature, such as a single nucleotide polymorphism (SNP), laboratory and/or tests and associated results, OTC (over the counter) or prescribed medications (current, past or prescribed for the current event), vaccinations, other past, current or prescribed therapies, diagnosis, discharge and admission dates, symptoms, demographic and geographic information (home, resident and/or work zip code, city, state, recent travel comments or observations), treating physician, workplace or other potentially toxic or hazardous exposures, and the like. As noted above, for some publication purposes, the patient personal identifier data can be removed from a message prior to its transmission to the Message Flow Server (or in some other embodiments, by the Message Flow Server) to comply with local Publisher and/or regulatory rules. It will be understood that this list of patient data is provided for exemplary purposes only and that embodiments of the present are not limited to the attribute types set out herein.

As further illustrated in FIG. 4, according to some embodiments of the present invention the application programs 154 include one or more of: a User/Participant Registry Module 120, a Publisher/Subscriber communication protocol interface module 124, and/or a Subscriber accessible and selectable electronic topic catalog module 125. The application programs 120, 124, 125 may be located in a local server (or processor) and/or database or a remote server (or processor) and/or database, or combinations of local and remote databases and/or servers.

As further illustrated in FIG. 5, according to some embodiments of the present invention the application programs 254 include one or more of a message format standardization module 220 that can convert, map and/or parse patient data into a patient message format, a Publisher Message Flow Server interface module 224, and/or a publication rule or constraint module 234 which allows a respective Publisher to define their own publication rules for their patient data. The application programs 220, 224, 234 may be located in a local server (or processor) and/or database or a remote server (or processor) and/or database.

While the present invention is illustrated with reference to the application programs 120, 124, 125 and 220, 224, 234 in FIGS. 4 and 5, respectively, as will be appreciated by those of skill in the art, other configurations fall within the scope of the present invention. For example, rather than being application programs 154, 254 these circuits and modules may also be incorporated into the operating system 152, 252 or other such logical division of the data processing system. Furthermore, while the application programs 120, 124, 125 and 220, 224, 234 in FIGS. 4 and 5 are illustrated in a single data processing system, as will be appreciated by those of skill in the art, such functionality may be distributed across one or more data processing systems. Thus, the present invention should not be construed as limited to the configurations illustrated in FIGS. 4 and 5, but may be provided by other arrangements and/or divisions of functions between data processing systems. For example, although FIGS. 4 and 5 are illustrated as having various circuits and modules, one or more of these circuits or modules may be combined without departing from the scope of the present invention.

FIG. 6 illustrates an exemplary environment for operations and devices according to some embodiments of the present invention. As illustrated in FIG. 6, the Message Flow Server 100 can comprise a part of a hub environment 10h. Generally stated, the hub environment 10h is configured to provide content based routing for Publishers to Subscribers. As noted above, the hub environment 10h may also be configured to transfer messages from Publishers to only authorized Subscribers to route approved content-based messages to publication-specific approved Subscribers. The system can allow participants to identify content, format and/or destination for the types of clinical information the wish to receive (Subscriber view) and/or they are willing to provide (Publisher view).

As shown in FIG. 6, the hub environment 10h may include an Administrative Server 1100 that is in communication with the Message Flow Server 100. The hub environment 10h may optionally also include an AGPI (Anonymous Global Patient Identifier) server 1109. The AGPI may be configured as a J2EE device. As is known to those of skill in the art, the J2EE is a Java™ 2 Platform, Enterprise Edition (J2EE) standard for developing component-based multi-tier enterprise applications (Java is a trademark of Sun Microsystems in the United States, other countries or both) It will be understood that the message server 100 and/or Administrative Server 1109 illustrated in FIG. 6 may include all or a part of the data processing system or database environment discussed above with respect to FIG. 4. The web-based administration server 1100, that, in some embodiments, can also be called a web-based administration application, can also be configured as a J2EE device. The hub environment 10h can also include other features, such as products available through•IBM's WebSphere® suite of products, such as a WebSphere Application Server, WebSphere MQ, a Tivoli® Directory server (LDAP) or "Lightweight Directory Access Protocol", and a DB2® UDB (a "DB2 Universal Database", which is a Relational Database Management System (RDBMS) that leverages the On-Demand features of IBM's eServer™ iSeries™). WebSphere, Tivoli, DB2, eServer and iSeries are trademarks of International Business Machines Corporation in the United States, other countries, or both.

Figure 9:
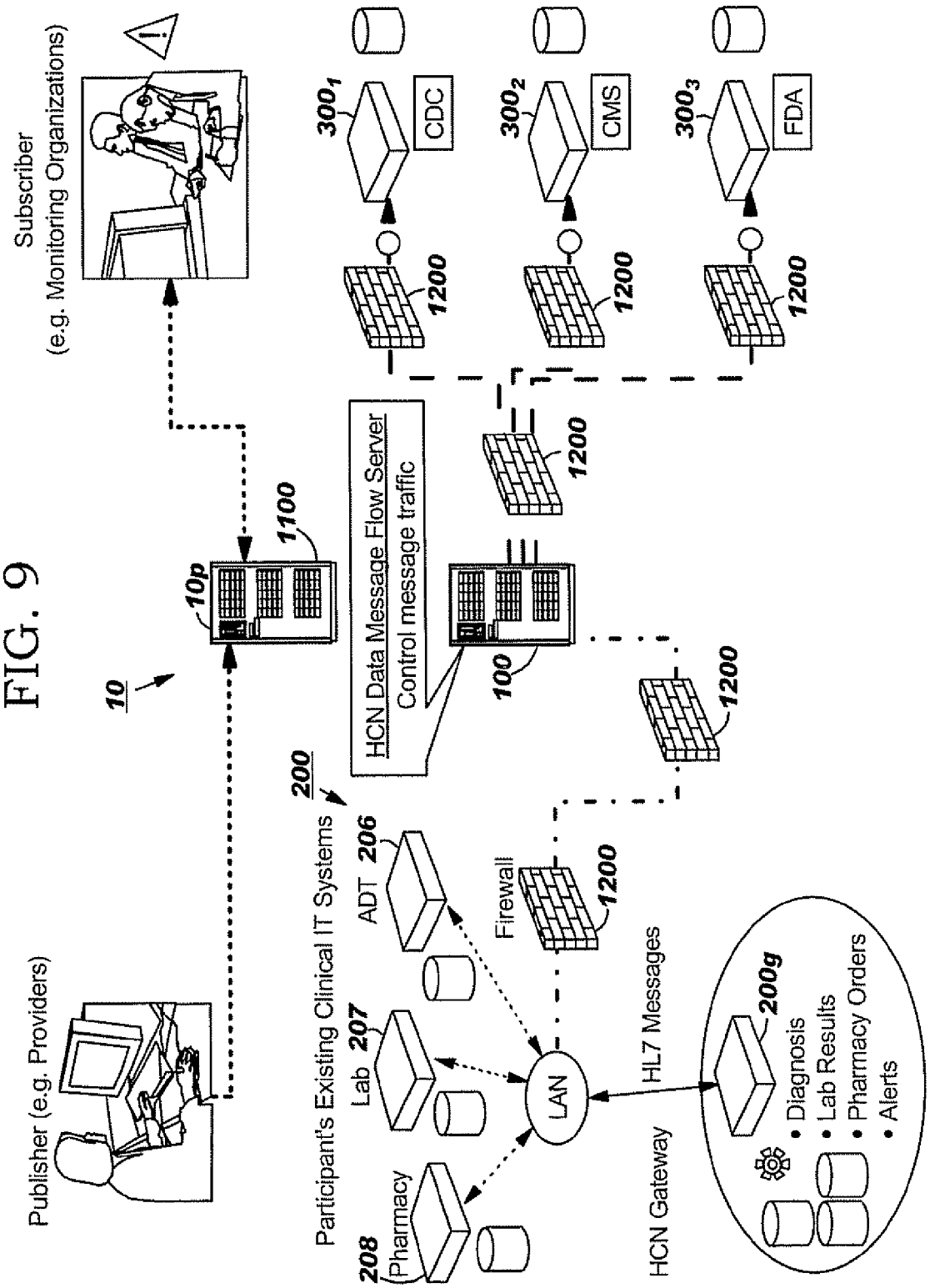
FIG. 9 is a schematic illustration of additional features of certain systems according to embodiments of the present invention.

FIG. 6 also illustrates that the hub environment 10h is in communication with a plurality of Publishers $200_1$, $200_2$, $200_n$ and Subscribers $300_1$, $300_2$, $300_n$. For a publication request for a particular selected topic from a Subscriber, $300_1$, the Administrative Server 1100 sends out notifications of requests for publication of the selected topic to one or more Publishers (shown as two Publishers, $200_1$, $200_2$) and receives responses back from those Publishers. The response can be a message approved for publication to the requesting Subscriber or a denial of the request. The response can also be cancellation of a previous (or standing) publication approval for a particular topic. The Message Flow Server 100 then sends all approved publication messages from respective Publishers to the requesting Subscriber $300_1$. The Administrative Server 1100 can pre-screen participants and levels of authorization or participation to send Subscriber requests only to potentially willing Publishers and the like. The messages to and from Publishers and Subscribers can be transmitted via the Internet using SSL (Secure Sockets Layer) channels, encryption and/or other secure data transmission means. The network system can include at least one domain firewall 1200. Typically, more than one firewall is used including hospital hub and Subscriber firewalls 1200 (FIG. 9).

Still referring to FIG. 6, the Publisher Gateways $200_1$, $200_2$, $200_n$ can be configured to connect to a respective Publisher participant's institutional computer systems and/or information technology systems to collect, aggregate and/or accept electronic data records that can be correlated to particular patients or other desired criteria. The Publisher Gateways $200g_1$, $200g_2$, $200g_n$ may also be configured to: (a) cache patient data for a desired time interval to allow for relevant data to be aggregated and/or compiled into a patient data record prior to publication or posting of a patient data message and/or prior to mapping the patient data to a patient data record message in standard message format; (b) de-identify or remove certain patient information from a patient record prior to publication (to provide anonymous and/or HIPAA privacy compliant data); (c) map and/or normalize messages, events and/or commonly accepted medical reference codes (such as Logical Observation Identifiers Names and Codes classifications "LOINC", International Classification of Diseases classification codes ICD-9, ICD-10, and the like) to convert local data to standardized formats; (d) perform message parsing such as parsing HL7 and XML data types; and (e) apply local business or data-use/publication rules.

In some embodiments, the Publisher Gateways 200 are configured to electronically correct electronic patient data records that have improperly formed HL7 messages, convert non-standard HL7 observation messages in electronic patient data records to standard HL7 messages, convert drug orders from a non standard HL7 observation to a standard pharmacy order message, map local Publisher codes for Admission Source and Discharge Disposition to HL7 recommended codes and/or data fields, and map local codes for laboratory observations to a generally accepted industry standard of laboratory tests/results (LOINC).

The Subscriber Gateways 300 can include or be in communication with a repository database in which they can store the publications of messages received in response to topical data requests (or for certain Subscribers or observers, a repository of messages and/or alerts).

In particular embodiments, the gateways 200, 300 can employ JAVA and/or IBM WBI code or other suitable program code. The Publisher Gateways 200 can include an XML-based patient "de-identification routine" that removes the personal identifiers (name, social security number and the like) from patient data messages. The Publisher Gateways 200 can also include: a document transform routine whereby patient data records are transformed from HL7 messages to CDA XML documents, HL7 parsing (a messaging HL7 toolkit which may be carried out using Chameleon from iNnterfaceware, located in Toronto, Canada), and Websphere Business Integration products, DB2 UDB, and HL7 TCP/IP sockets to WBI Connectors.

FIG. 7 illustrates that the Publisher and Subscriber Gateway 200g, 300g can be provided as a common gateway 200gc that implements both functions. FIG. 7 also illustrates that the AGPI (Global Patient Registry or Identifier) server 1109 can communicate directly with Publisher Gateways 200g to provide a common patient registry service to the respective Publisher Gateways 200g.

Figure 8:
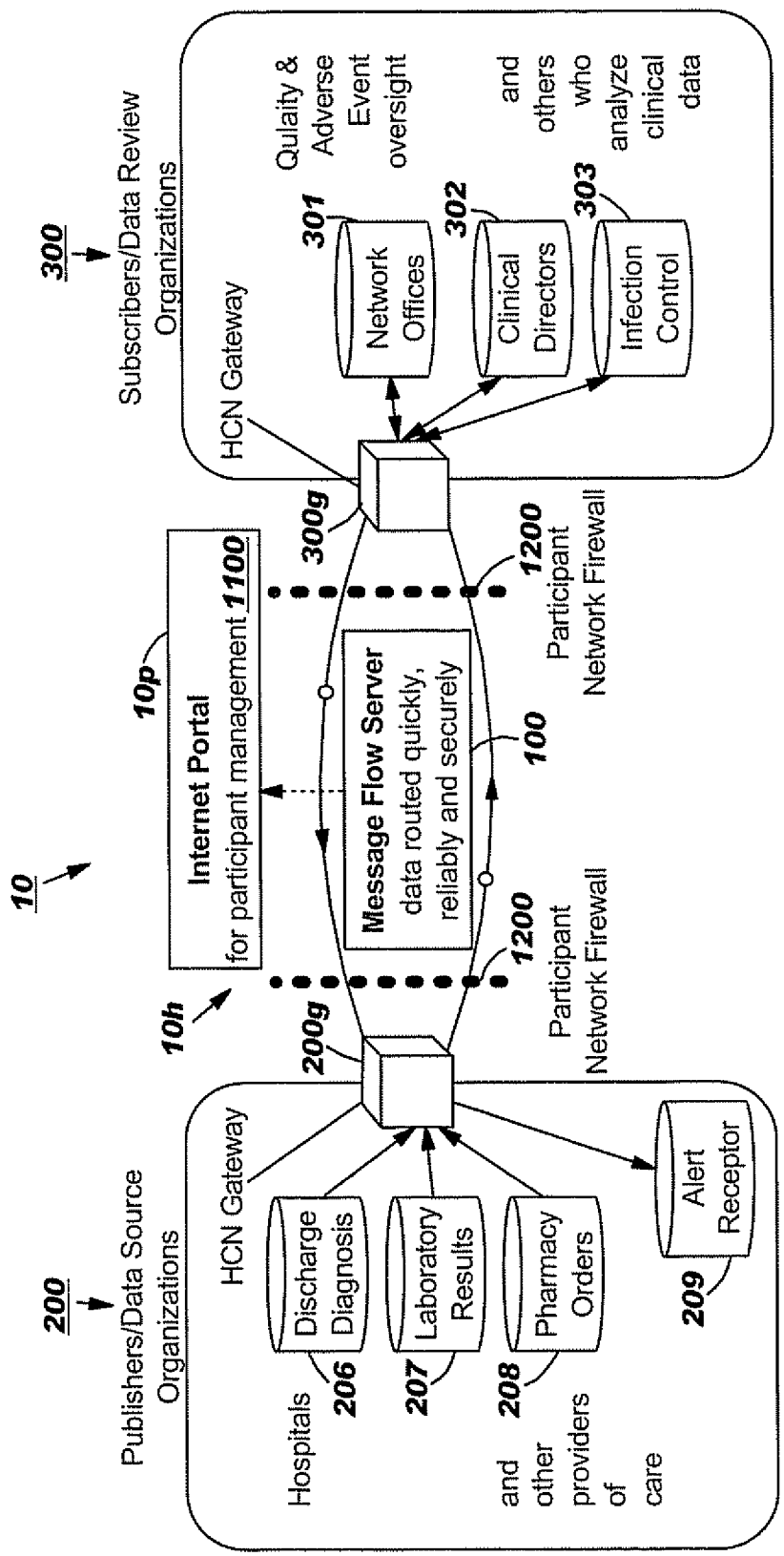
FIG. 8 is a schematic illustration of exemplary system architecture for a networked system according to embodiments of the present invention.

FIG. 8 illustrates an exemplary architecture for a collaborative data network system 10. The system 10 includes an Internet portal or hub 10h with the Message Flow Server 100 and participant network firewalls 1200. As shown, each Publisher site 200s can include at least one Publisher Gateway 200g that communicates with various linked (internal and/or external) service providers or data collection stations, such as, but not limited to, a hospital billing system 206 (which can provide a discharge or intake diagnosis), laboratory 207 (that can provide laboratory or test results or tests/evaluations ordered), a pharmacy 208 (for input of drug orders), and other relevant data collection inputs. The Publisher Gateways 200g can be configured to filter, link and map healthcare data elements based on Publisher-specific business rules or constraints that they select, approve and/or define.

One example of a business rule can be that patient records are checked to see if all recommended tests or procedures have been completed based on a diagnosis. Also the system can identify patients diagnosed with a certain disease or impairment and correlate the follow-up lab results to confirm the diagnosis. These checks or rules can drive patient care improvements, facilitate proper treatment and/or help manage disease outbreaks. In some embodiments, the results or data summaries of the patient records can be shared within an organization rapidly and reliably using WebSphere MQ from IBM. The system 10 can be used to track outcomes in a rapid and error-reduced or error-free manner that is better than conventional chart-pulls that are delayed or prone to more errors. This type of automated reporting can facilitate compliance with audit plans or requirements.

The Gateway 200g can be in communication with an alert receptor 209 whereby data gathered and/or provided by the Gateway 200g can be electronically monitored to generate an alert to internal authorities and/or administrators when certain abnormal conditions are identified. The alert receptor 209 can be a separate module and/or database at a Publisher 200 that communicates with the Gateway 200g or can be integrated into the Gateway 200g. For example, the alert receptor 209 can detect a rise in the number of patients admitted for a certain condition and/or identify possible widespread health concerns, such as a food poisoning diagnosis, identification of an anthrax exposure or spinal meningitis in one or more patients, a bioterrorism exposure, an increase in prescriptions for a certain drug or drug type (such as those identified as addictive or with higher mortality risk), adverse drug events and the like.

FIG. 8 also illustrates that a Subscriber (organization or site) 300 can include one or more affiliated entities (that may be local or remote with respect to each other) that can provide quality and/or adverse event oversight or analyze clinical data and connect to a Subscriber Gateway 300g. As shown, a Subscriber 300 can include a network office(s) 301 and clinical director(s) 302, and infection control official, organization/entity 303. The Subscribers can create a topic (define the parameters of the data requested) and subscribe and/or select a topic (define a respective Subscriber's specific interest in a topic).

As noted above, the Subscriber site and the Publisher 200 can be a common Publisher and Subscriber site that employs a common gateway 200c (FIG. 7) that can act in either a Publisher or Subscriber mode. The alert receptor 209 and Publisher Gateway 200g and/or the Subscriber 300 can be used to monitor patient care processes and quality of care and can be used to generate reports such as that shown in FIG. 12.

FIG. 9 is a schematic illustration of different components in an exemplary collaborative healthcare data sharing system 10. As noted above, the system 10 can include a web portal 10p that controls participant access and communicates with the Message Flow Server 100 that controls message traffic. The web portal 10p may be a single federated or even global portal or a linked system of several portals, such as separate portals for foreign or selected networks, and the like. The system 10 allows participants to define data sharing rules, select what data to share and decide with whom to share, and monitor, alert, notify, and report on selected topics and provide account activity.

Figure 10:
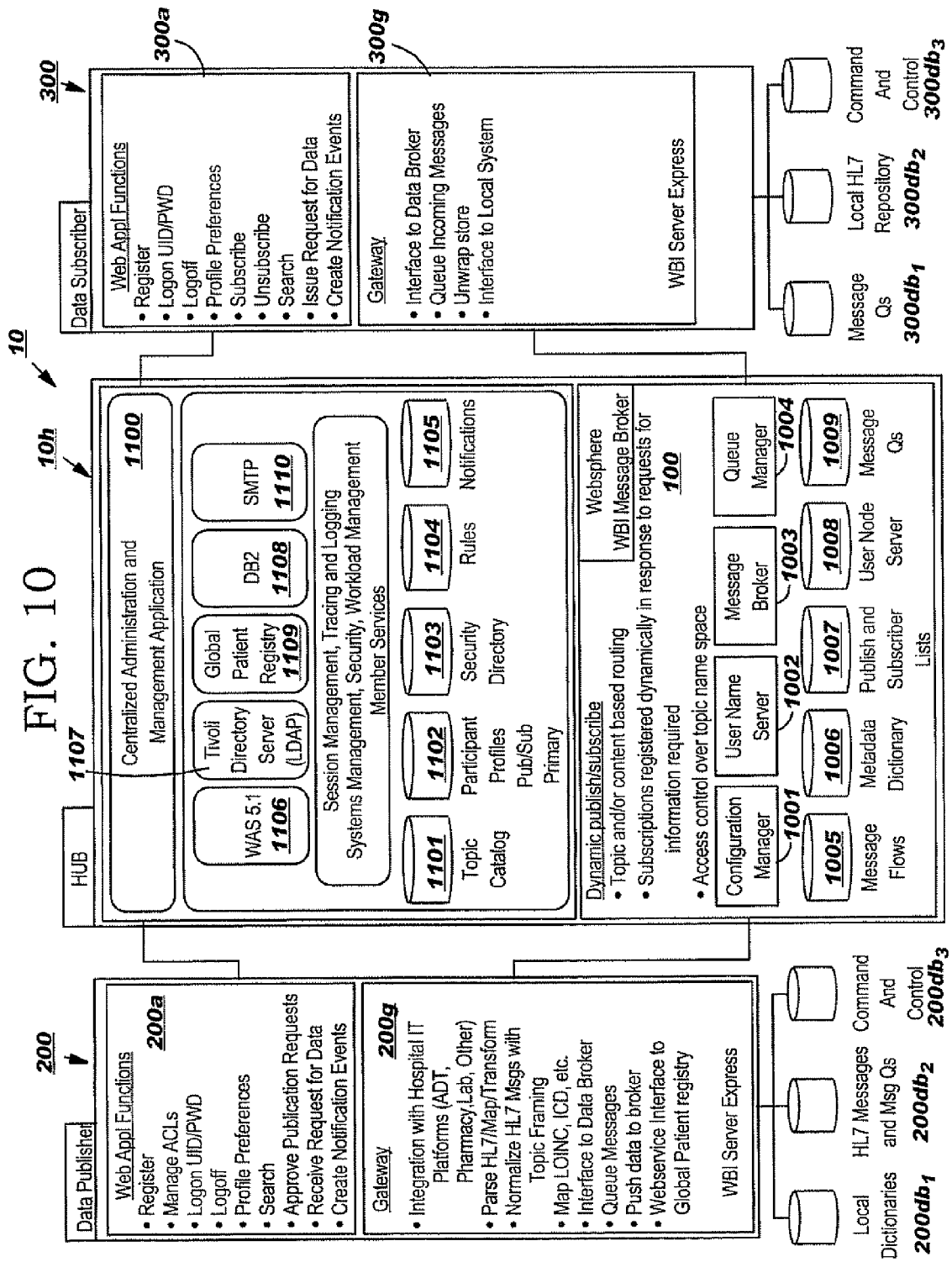
FIG. 10 is a schematic illustration of a system that includes a hub that interfaces with Publishers and Subscribers according to embodiments of the present invention.

FIG. 10 illustrates a more detailed architecture of an exemplary web based data sharing system 10 according to some embodiments of the present invention. As shown, the hub 10h comprises a server 1100 that provides a centralized administration and management application. The Administrative Server 1100 can be configured to provide session management, tracing and logging systems management, workload management and member services. The Administrative Server 1100 can include or communicate with a plurality of databases including: a topic catalog 1101, participant (Subscriber and Publisher) profiles 1102, a security directory 1103, publishing or routing security rules 1104 and notifications 1105. The Administrative Server 1100 can include several sub-servers for integration into web systems, such as, but not limited to, a WAS (web application server) which may comprise an IBM WebSphere Application Server, a Tivoli Directory Server (LDAP), a AGPI (Global Patient Registry or Identifier) Server 1109, a DB2 Server, and a SMTP (Simple Mail Transfer Protocol) Server 1110. It is noted that although described herein as "servers" other suitable computer configurations may be used.

The topic catalog database 1101 (FIG. 10) can be an electronic catalog or listing of Subscriber selectable topics (which may include a topic name and a topic description) such as those shown in FIG. 15. The topic catalog can be presented in alphabetical order (such as when a complete listing is provided) or may be searchable using a key work input as also shown in FIG. 15. If a Subscriber wants to request data for a topic that is not in the catalog, the Subscriber can enter the request as a "new" topic entry that can be saved and reviewed to see if it meets publication rules. Once in the catalog, a Subscriber can request data on that topic, but the hub 10h (either the Administrative Server 1100 or the Message Flow Server 100) can select which (if any) Publishers to send the request to publish healthcare data on the new (or existing) topic based on previously established Subscriber and/or Publisher participation rules and the like.

Figure 16A:
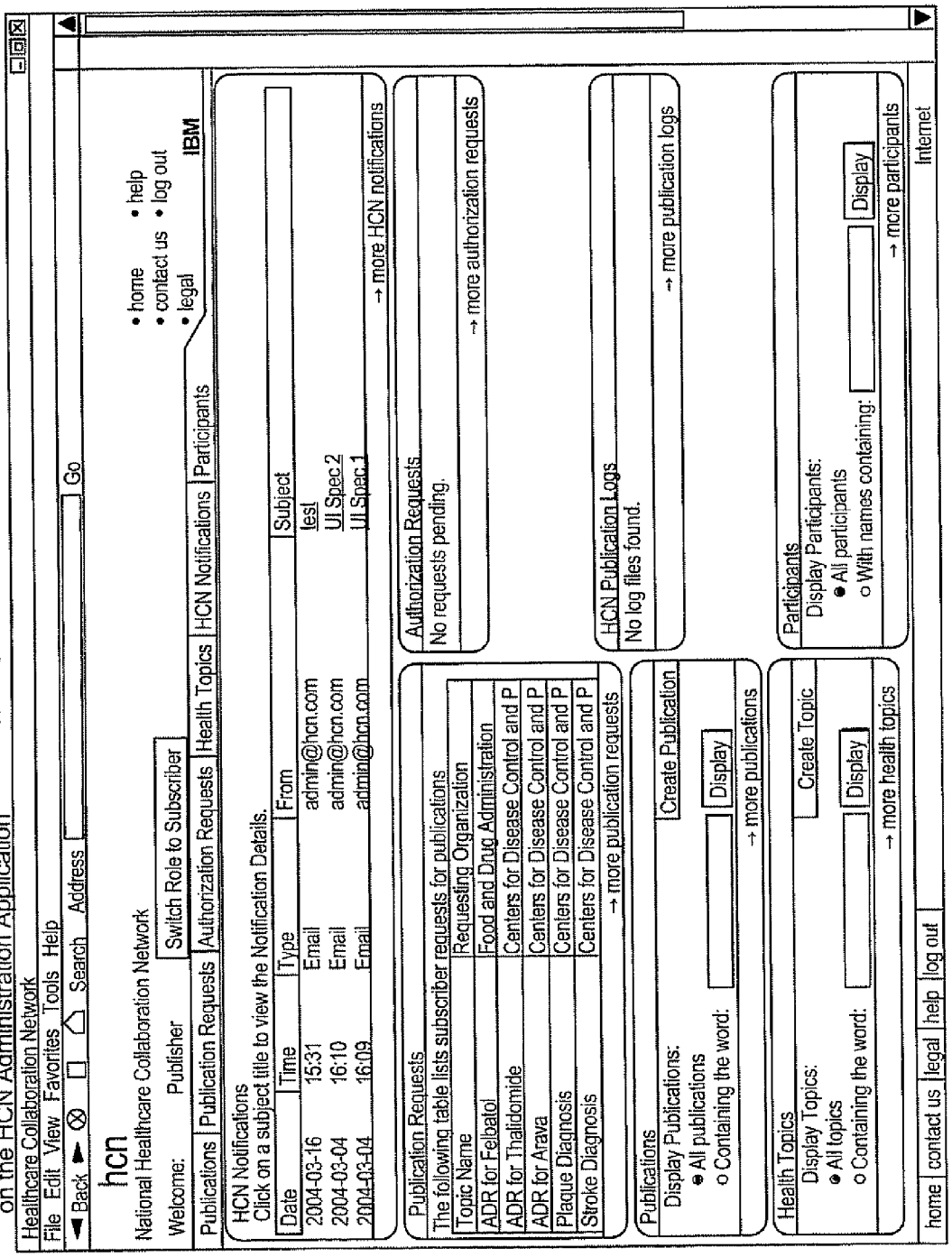
FIGS. 16A and 16B are screen printouts of an exemplary Publisher "home" view from/on an administration application according to embodiments of the present invention.

The notifications database 1105 can be used to provide a notification summary such as shown in FIGS. 14 and 16A. As shown in these figures, a Publisher can view notification details including date, time, type, from, and subject. The Publisher can also review publication requests, which provide a requesting Subscriber's identity/name and the requested topic. The screen views shown in FIGS. 14 and 16A can be configured as a Publisher "home" screen view.

Referring again to FIG. 10, the Message Flow Server 100 can be configured to dynamically publish and/or subscribe selected topics of interest from participating Publishers to participating (approved) Subscribers and implements the publish/subscribe communication protocol. The Message Flow Server 100 can comprise a message broker such as a WebSphere WBI (WebSphere Business Integration) message broker that can provide topic and/or content based routing, register subscriptions dynamically in response to requests for selected information, and provide access control over a topic name space. The Message Flow Server 100 can include one or more sub-servers, clients or managers, such as, but not limited to, a configuration manager 1001, a user name server 1002, a message broker 1003, and a queue manager 1004. The Message Flow Server 100 can comprise and/or communicate with several databases or servers, clients and the like, such as, but not limited to, a message flow database 1005, a metadata dictionary 1006, publish and Subscriber lists 1007, user node server 1008, and a message queue database 1009.

As also shown in FIG. 10, the Administrative Server 1100 can be configured with web application functions that appear at Publisher portal sites 200s. The server 1100 may comprise and/or be configured as a WBI servers express. The web application can be used to: allow a user to register as a participant, manage ACLs (Access Control Lists), logon UID/PWD (using universal ID or password access), logoff, define profile preferences, search, approve publication requests, receive request(s) for data, and create notification events.

The Publisher Gateway 200g can be configured to integrate with hospital or other Publisher IT (information technology) environments or platforms such as pharmacy, lab, and ADT (Admission, Discharge and Transfer) and the like. The Gateway 200g can also be configured to parse HL7/map/transform, normalize HL7 messages with topic framing, map LOINC, ICD codes, interface with the Message Flow Server 100 at the web portal, queue messages, push data to the data broker, provide a webservice interface to the Global Patient Registry 1109 at the hub 10h. The Gateway 200g can be in communication with and/or comprise a plurality of databases, such as, for example, a local dictionary or dictionaries 200$db_1$, HL7 messages and message queues 200$db_2$ and a command and control database 200$db_3$.

Table 1 illustrates exemplary HL7 supported events with a topic description and associated code.

TABLE 1

Currently Supported HL7 Events

| | |
|---|---|
| ADT A01 | Admit a patient |
| ADT A02 | Transfer a patient |
| ADT A03 | Discharge a patient |
| ADT A04 | Register a patient |
| ADT A08 | Update a patient |
| ADT A09 | Patient Departing |
| ADT A11 | Cancel Admit |
| ADT A13 | Cancel Discharge |
| DFT P03 | Detailed Financial Transaction |
| OMP O09 | Pharmacy/Treatment |
| ORM O01 | General order |
| ORU R01 | Observation Result |
| RDE O11 | Pharmacy/Treatment encoded order |
| RDS O13 | Pharmacy/Treatment dispense |
| VXU V04 | Vaccination Record update |

Additional HL7 messages can be implemented as part of a configuration as desired.

FIG. 10 also illustrates a Subscriber portal site 300s that communicates with web application functions 300a. As for the Publisher site, all or some of the web application functions can be carried out by the Administrative Server 1100. The web application functions can be used to: allow a Subscriber to register as a participant, logon UID/PWD, logoff, define profile preferences, subscribe, unsubscribe, search, issue request for data, and create notification events. The gateway 300g can be configured to interface with the Message Flow Server 100 at the web portal, queue incoming messages, unwrap store and interface to a local IT system. As shown, in FIG. 10, the gateway 300g can include or communicate with a plurality of databases including a message queue database 300$db_1$, a local HL7 repository of received messages 300$db_2$, and a command and control database 300$db_3$.

Figure 11:
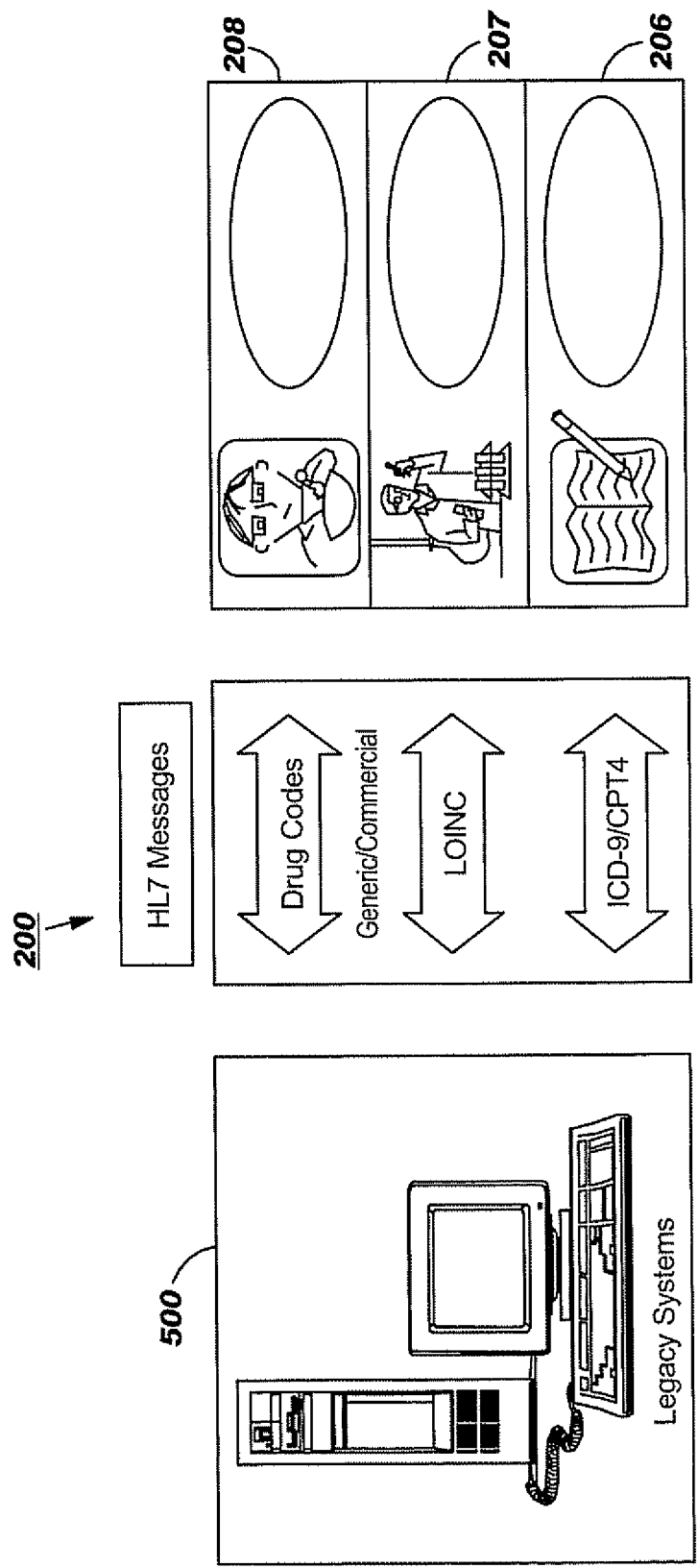
FIG. 11 is a schematic illustration of a message integration system of patient record data according to embodiments of the present invention.

FIG. 11 illustrates an existing healthcare Publisher site 200s with a legacy or existing IT system 500 and different codes or classification systems used within that environment. For example, the site 200s the pharmacy 208 can use drug codes (generic/commercial), the lab 207 can use LOINC codes and the administrative input records 206 (admission, discharge and transfer or patient care records) can use CPT4 codes. These disparate codes/classifications can be converted into a standard message format, typically using HL7 messages.

Table 2 illustrates data elements that can be monitored and/or tracked using messages according to some embodiments of the present invention.

| DATA ELEMENT | DISEASE STATE |
|---|---|
| General | |
| Admitting Diagnosis | All |
| Discharge Diagnosis | All |
| Discharge Disposition | All |
| Gender | All |
| Admission Source | All |
| Race | All |
| Diagnoses | |
| Anthrax Diagnosis | Anthrax |
| Legionella Diagnosis | Legionella |
| AMI Diagnosis | AMI |
| Diabetes Diagnosis | Diabetes |
| Stroke Diagnosis | Stroke |
| Pneumonia Diagnosis | Pneumonia |
| Observations | |
| Respiratory Viral Results | Respiratory |
| Varicella Test Results | Varicella |
| HDL Cholesterol | Diabetes |
| LDL Cholesterol | AMI, Diabetes |
| Triglycerides Result | Diabetes |
| Positive Pregnancy | Adverse Drug |
| Medications | |
| ACE Inhibitors | AMI |
| Antibiotic | Pneumonia |
| Felbatol | Epilepsy |
| Thalidomide | Leprosy |
| Antithrombotic | Stroke |
| Nifedipine | Stroke |

The examples are for illustration only and are not to be limiting to the scope of the invention, as the types of topic data categories and elements are not limited to those shown in the examples.

Figure 12:
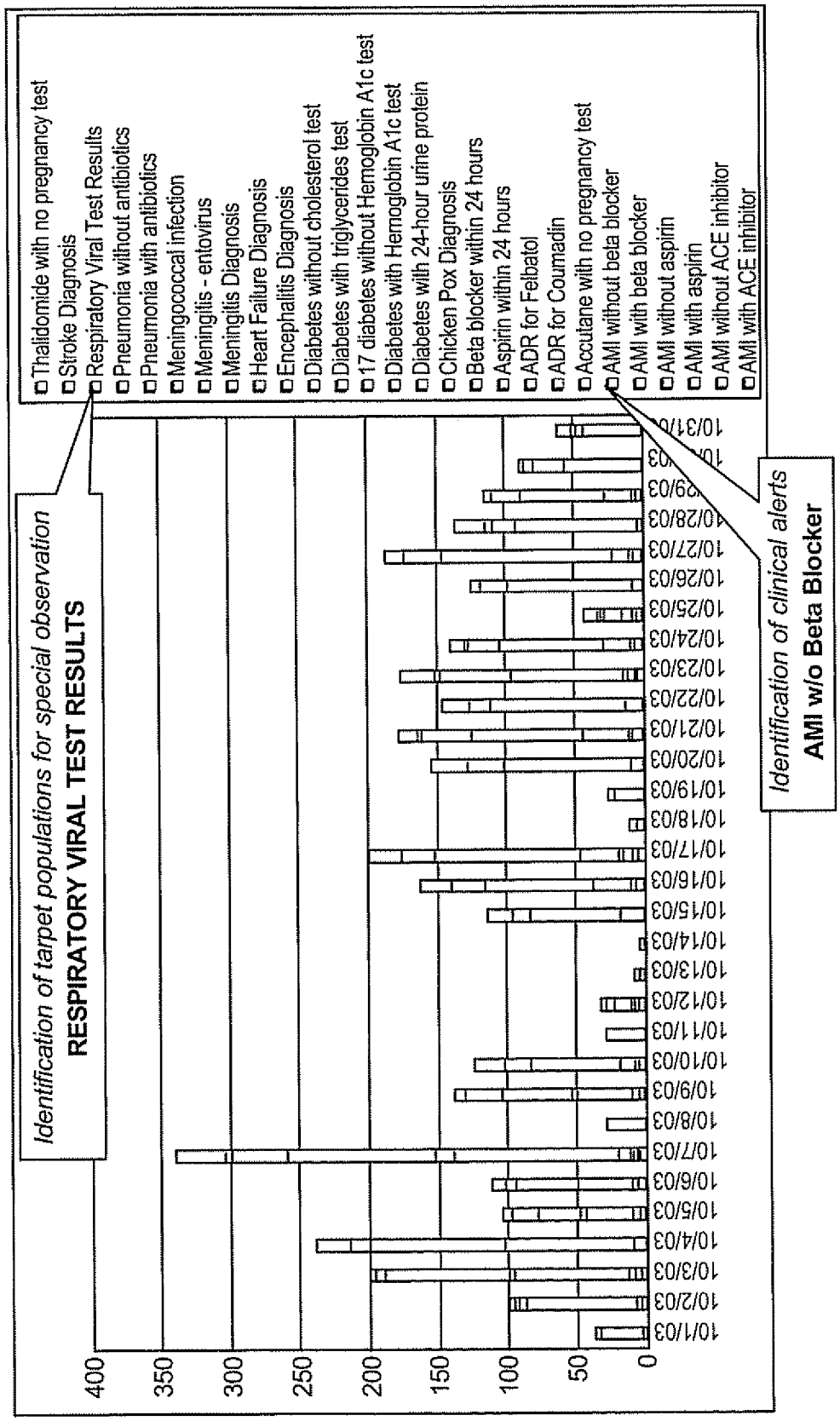
FIG. 12 is a graph of a data summary of topical events that can be generated according to embodiments of the present invention.

FIG. 12 illustrates that a data flow summary of different events that can be compiled for oversight or business needs or desires of a particular participant. As shown, a chart of aggregate messages by date and type of event/healthcare issue can be provided. Such information can be used to identify target populations that may be flagged for special observation (such as respiratory viral test results), or generate clinical alerts (such as when a patient with Acute Myocardial Infarction has not been identified as ordered a beta blocker medication within a certain time frame from admission). The reports can be customized and/or automatically generated according to different local uses. FIG. 15 illustrates a sample view of an activity summary at a Publisher Gateway 200g using the portal 10p to view internal, Publisher-specific messages by topic name.

Table 3 illustrates some examples of "key" data elements that can be tracked by a participating agency, particularly a governmental agency, to evaluate quality of care and/or trends in health.

TABLE 3

| KEY DATA ELEMENT | ADDITIONAL |
| --- | --- |
| Observations | |
| AMI Diagnosis (GE 65) | All Labs and Med Info |
| AMI Diagnosis LT 65 | All Labs and Med Info |
| HF Diagnosis GE 65 | All Labs and Med Info |
| HF Diagnosis LT 65 | All Labs and Med Info |
| Pneumonia Diagnosis GE 65 | All Labs and Med Info |
| Pneumonia Diagnosis LT 65 | All Labs and Med Info |
| Meningitis | All Labs and Med Info |
| Medications | |
| Coumadin | Pro thrombin time |

FIG. 13 is an example of a message 200m that includes three data message segments, lab data 200l, pharmacy data 200p and diagnosis data 200D for a patient. The message 200m was approved and submitted for publication to the Message Flow Server 100 for transmission to the requesting Subscriber(s). The message identifies the topic "Stroke Diagnosis" and includes an associated rule name of "Stroke Diagnosis", a Provider identifier and a Global patient identifier number (Patient ID) with a message time stamp.

Figure 16B:
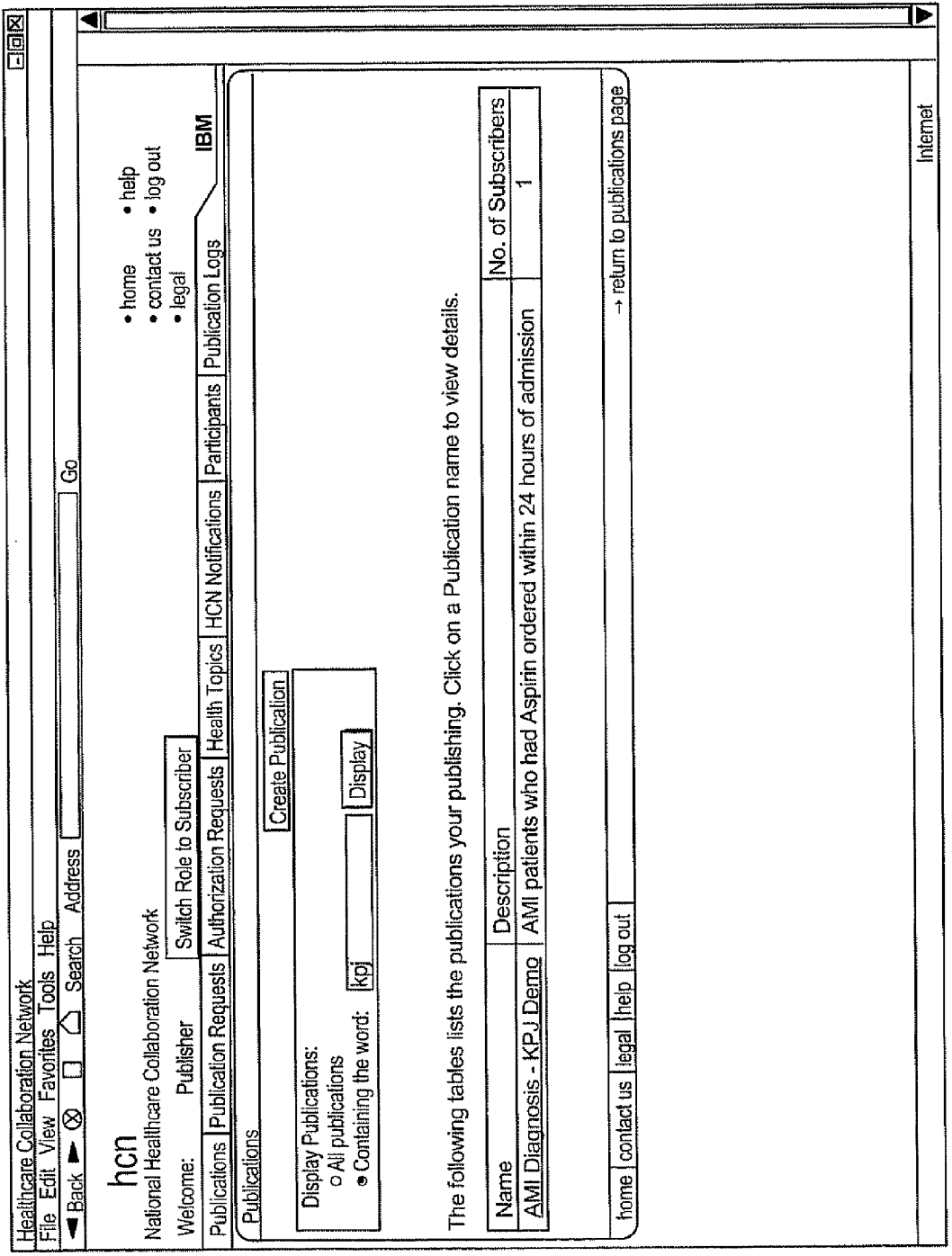

FIG. 16A illustrates the Publisher viewing and use mode and FIG. 16B illustrates that under a publication mode, a Publisher can view publications that are publishing with the details of same (and a Publisher can cancel the publication if desired). The Publisher can create a publication (agree to provide data for a topic subscription), view publications (list the details of publications—all or select records), and delete a publication (allows the Publisher to delete an existing publication). The participant Publishers can generally stream all supported data to their gateway 200g on a continual basis for all patients. The clinical systems can generally stream (send) the data in the form of HL7 messages. Their respective gateways 200 can store their patient messages for a desired time as noted above.

FIG. 17A illustrates that a user can electronically select to go to a Subscriber mode. FIG. 17A illustrates some details of a selected topic ("topic definition details") that a Subscriber can identify or select to obtain healthcare records of interest (if the Subscriber is authorized for same according to defined rules). The topic includes a topic trigger event (shown as a disease diagnosis of "AMI" or acute myocardial infarction), items of interest (shown as a drug order of aspirin) so that only records that indicate matching drug order will be included in the returned data, and whether demographic data is of interest or whether the request is further limited by same. Once a topic is created and stored in the topic catalog, it can be used by all Subscribers as long as their respective use entitlement (privacy provisions or entitlements) are compatible with the topic.

The system 10 provides filters that allow a participant to limit the content of data sent. By default, typically, all filters are applied and the Subscriber will receive data for all types of data supported by the system. The participant can "turn off" or deselect one or more filters. In such case, the system 10 can send data matching the topic events and data for categories that were not filtered.

The primary purpose of a "topic event" function is to select patient records with relevant data. The topic event function can also impact the content of the data. For example, a first occurrence of any topic events marks the begin bracket for messages to be sent and the first occurrence of the last topic event marks the end bracket of messages that will be sent. The order in which topic events are matched is generally not considered. All messages which occur between the start and end bracket will be sent if other rules do not override this procedure. If a topic event is a diagnosis, the begin bracket can be admission and the end bracket discharge (typically the entire patient encounter). The Subscriber can limit duration by specifying a time duration. If duration is identified, then the evaluation begins with admission and ends with the time limit is reached. If all topic events and specified demographic data are not matched during the time specified, no data message record will be sent. Data can be sent when all topic events are matched. Typically, however, a participant cannot specify when data is to be sent.

Figure 17B:
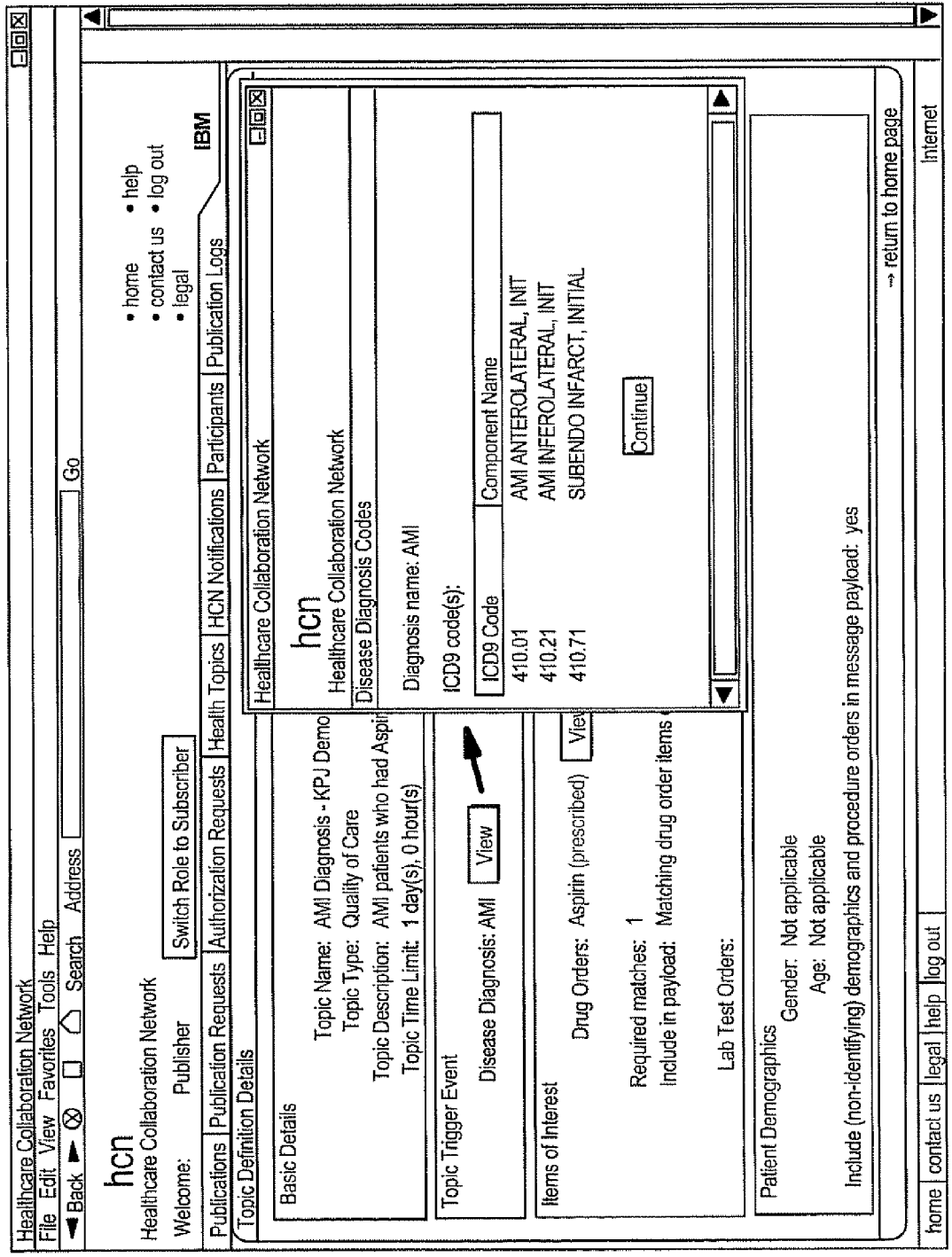
Figure 17C:
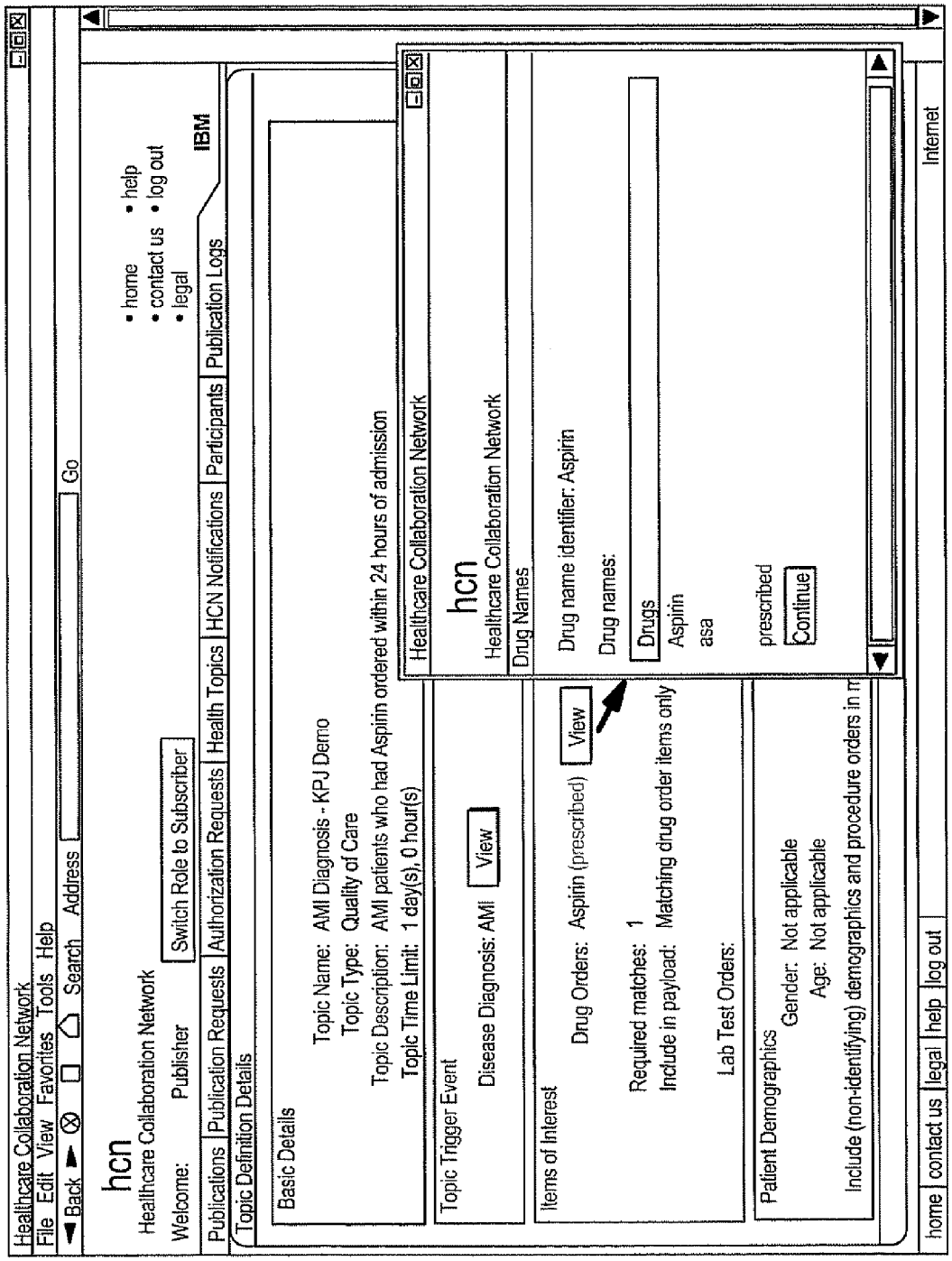

Once a trigger event is received at a Publisher from a Subscriber (via the Message Flow Server 100), the Publisher evaluates stored messages and subsequent messages for a patient to see if the patient(s) exhibit all specified criteria FIG. 17B is a screen view of further information regarding the trigger event field that can be accessed via the "view" button. As shown, for the diagnosis name "AMI" is associated with three ICD-9 codes, 410.01, 410.21 and 410.71. Records matching one or more of these codes can be included based on this requested trigger event. For a diagnosis, the participant should define all related variations and valid ICD-9 codes. Similarly, FIG. 17C illustrates further information regarding the aspirin drug order can be obtained via the associated view button. As shown, for a drug name identifier of "aspirin", records that have drugs prescribed under "aspirin" or "asa" will be included.

Typically, the system 10 can receive lab and procedure observation/result messages that contain the order ID and associated LOINC, CPT or ICD-9 code from the order. If participants (Subscribers) want data regarding lab or procedure orders, a lab or procedure result should be specified as a topic event category for additional data. If an event is defined by a lab result, the participant should specify all desired variations of the lab test using corresponding LOINC codes. The participant can also specify results criteria under topic events. If the event is a procedure, the participant should specify all desired variations of the procedure that are valid values for each procedure specified and should have a corresponding valid ICD-9 or CPT code. The participant can specify if ICD-9 and/or CPT codes should be used.

Embodiments of the invention can be used to automate quality and compliance reporting as well as clinical data sharing with federal and state agencies like the CDC (the Centers for Disease Control), the FDA (Food and Drug Administration), the NIH (the National Institutes of Health) and the CMS (the Centers for Medicare and Medicaid). Other federal agencies that may potentially participate in collaborative data sharing systems include the DOD (Department of Defense), the FAA (the Federal Aviation Agency, the FBI (Federal Bureau of Investigation), the Department of Homeland Security and the like. In some embodiments, the systems of the present invention can harness existing electronic data available in many provider settings, such as ICD, CPT, LOINC, and NDC via HL7.

FIG. 18 illustrates that embodiments of the present invention can be used to identify adverse drug events (ADE). The gateway 200g can be configured to identify adverse drug events. In some embodiments, the message data for an identified adverse drug event can be held in a dedicated database and/or alert receptor (FIG. 8, 209). Upon detection of an ADE at a Publisher site 200$_2$, an automated electronic alert 200A can be sent by the hub 10h to other Publishers 200 and/or Subscribers 300. The alert 200A can be formatted as a message integrated alert that is sent to selected participants using constraint-based rules. The rules can be set to selectively send the alert 200A to Subscribers of an associated health topic in the topic catalog. Examples of Subscribers may include the treating physician and/or hospital, a manufacturer of the drug, a clinical trial administrator, a competing manufacturer of a different alternative drug, or a governmental agency (the CDC, the FDA and the like) in generally real time using a messaging system as described above.

FIG. 19 illustrates that embodiments of the present invention can be used to monitor and/or identify disease outbreaks. As for the ADE alerts, disease outbreaks, certain diagnosis or exposure observations can trigger a disease/ exposure alert 200A' to all or some of the participating Subscribers 300. As before, the alerts 200A' may be sent based on constraint-based rules to selected Subscribers. For example, some participating Subscribers (such as governmental agencies) may be particularly interested in prompt notifications when Publishers identify patients having diseases or exposures associated with increased mortality rates, public health risks, diseases that are considered contagious, increased numbers of patients having common diagnosis (abnormal outbreaks) and/or bioterrorism events or agents. For example, the system can monitor and identify new or unexpected increases in viral, bacterial and/or protozoan caused diseases including, but not limited to, typhoid, tuberculosis, polio, small pox, a plague (bubonic), ebola, marburg, avian flu, West Nile Virus, SARS (severe acute respiratory syndrome), hepatitis and HIV. The system can also monitor and identify for bioterrorism events or agents or environmental hazards, such as anthrax exposure, food poisonings, *e coli* exposures, Creutzfeldt-Jakob Disease, radiation exposure, ricin exposure, asbestos exposure, and lead exposure. A more complete list of potential bioterrorism agents can be found at the CDC website: www.bt.cdc.gov/ agent/agentlist.asp The alerts 200A' can be sent in substantially real time from a Publisher source 200 via the hub 10h to the Subscriber 300. In particular embodiments, the periodicity of the data transmission from a Publisher to one or more approved Subscribers can vary according to a Subscriber's request and/or a Publisher's collection of relevant data. A Publisher 200 can be configured to stream patient data and correlate the data generally or substantially continuously (and may do so continuously, ignoring computer or power disruption or outages) so that a suspect disease can be promptly identified upon admission, lab test and/or discharge.

The monitoring can be used to provide generally real-time disease monitoring for regulatory agencies and/or payors, such as insurance companies. Early detection and monitoring by payors may allow patients to be placed in appropriate or more aggressive treatment programs or therapies, potentially reducing healthcare costs, particularly for diseases where early detection and disease management are beneficial to reduce costs, increase longevity and/or decrease mortality rates.

Embodiments of the invention can be used to integrate patent data across disparate (inter and intra) clinical systems, provide clinical quality reviews and oversight and potentially reduce the number of errors that can arise during medical treatment. The systems can be used to monitor clinical performance, process variation and provide business related data such as cost analysis. A single Publisher can support multiple Subscribers and publish clinical data in different formats as discussed above (such as using HL7 messages, short text messages, emails and the like) and publish to different devices such as PDA's, personal computers, mainframes (directly to repository databases), portable wireless communication devices cellular phones/communications and the like.

The publishing sites (data source organizations) can control publication of its own patient data and approve or deny a Subscriber (data review organization) request for data. Publishers can comply with HIPAA privacy regulations by transmitting patient data (non-directly identifiable patient data as appropriate) using high security standards around authentication and encryption.

The systems can integrate pharmacy, laboratory and admission/discharge systems and collect relevant data streams (such as HL7 data streams) and correlate the patient data so that a relatively comprehensive record can be forwarded to an approved Subscriber. The system is configured to control and/or verify that only approved data is securely published in an agreed-upon manner (such as without patient identifier data).

The systems can use a "publish and subscribe" protocol that routes requested data based on content (clinical topics for healthcare systems) and a subscription entitlement that is linked to a privacy and/or authorization level. The architecture is relatively flexible, scalable and configured to facilitate easy adoption at participant sites.

FIGS. 20, 21A, 21B and 22 illustrate embodiments of privacy-level data sharing protocols that may used to provide secure data sharing between Publishers 200 and Subscribers 300 according to embodiments of the present invention. That is, the system 10 can be configured with protocol level security to allow only authorized users to participate in the data sharing network to prevent external unauthorized users from accessing or tampering with data. In addition, the system 10 can employ an "entitlement" privacy level protocol that blocks Publishers 200 of data from sending data to Subscribers 300 that are not authorized and/or entitled to receive all or certain types of data.

Figure 20:
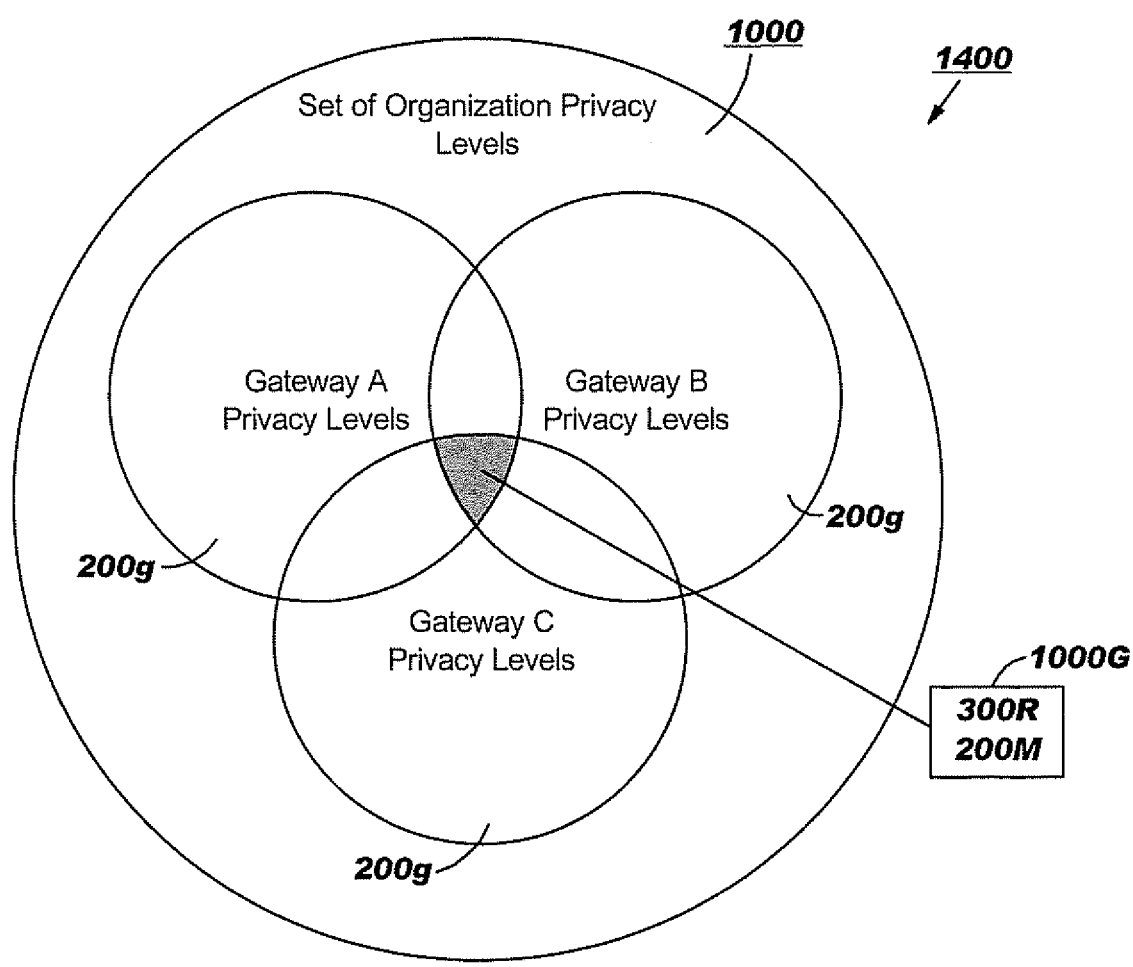
FIG. 20 is a schematic illustration of a Privacy Level grid according to embodiments of the present invention.

FIG. 20 illustrates a privacy level grid 1400 that defines a system set of privacy levels that an organization may have. The term "organization" may be thought of as a group of affiliated departments and/or entities, a set of non-affiliated entities or persons, and/or even the entire system 10 itself. A given network can be configured with a central Privacy Register so that all clients can reference a single authority on the meaning of a given privacy level and a common set of privacy levels with common definitions for entitlement and/or data sharing protocols can be defined for the network or system (i.e., within an application Domain). The term "privacy levels" refers to a classification system that classifies types of data according to lesser to greater degrees of content or patient-identifier data (i.e., data that is deemed more generic versus data that is deemed to be sensitive, personal and/or "secret" data). The privacy levels may be configured to allow access to a larger or different data content. In other embodiments, the privacy levels may be configured in a hierarchical manner such that a greater privacy level may include the right to access data having lower privacy levels. In some embodiments, the privacy levels can be configured to define an entitlement for Publisher Gateway filtering and/or Subscriber access to discrete data content, i.e. data records with patient healthcare as well as patient-identifying information.

A particular client (i.e., Subscriber and/or Publisher) can support either the full set or a subset of the defined privacy levels for a particular network or system for data sharing. Thus, for example, a Subscriber 300 cannot support (request or create data) on topics that are outside an assigned privacy level(s) and a Publisher Gateway 200g cannot publish (or in some embodiments, even compile) data records that are outside its particular assigned privacy level(s). A respective Publisher Gateway 200g (or, indeed Subscriber Gateway 300g) is not required to support the complete superset of defined privacy levels within an organization 1000, but the respective Gateway 200g should support the privacy level for the portal to which they report.

Generally stated, only electronic data records 1000G (which may be defined according to topics) that comprise data content at a privacy level that is at the intersection of the different privacy levels of all the different Gateways 200g can be allowed to be "global" (i.e., all Subscribers may request data 300R and all Publishers may transmit publication data 200M for a global data topic) for a particular organization. A global privacy level can be permissively used/supported by all Gateways 200g, 300g and/or participating organizations. Other data requests will not be globally available to all users. For healthcare data sharing embodiments, one defined privacy level can be "HIPAALimited A" and another can be "HIPAAFullyDeidentified", each having data sharing constraints that correspond to the legal rules which define these levels. In other non-health fields, different data sharing constraints and privacy levels can be used.

Typically, during "on-boarding" or customer set-up, a client (whether Subscriber or Publisher or other) is brought into the network or system 10 and assigned one or more privacy levels based on local participant data sharing decisions or choices and/or a legal entitlement to send and/or receive certain types (and/or content) of data. Where a respective Publisher 200 has more than one Publisher Gateway 200g, each Publisher Gateway 200g may support a different privacy level. A Publisher Gateway's 200G or Subscriber's 300 respective privacy level(s) is assigned for one or a set of privacy levels that define their legal right to provide or access data included in that level. For example, in some particular embodiments, the Subscriber participant can be defined as an exempt, non-exempt, internal, external or governmental participant and the like. The privacy levels can be alternatively defined or established in a given system installation/application. Certain governmental Subscribers 300 may have an entitlement that allows them to view "fully-identified" patient data. The system 10 can be configured so that a participant can only communicate with other participants that operate at or support their assigned privacy level(s). When Subscribers 300 and/or Publishers 200 wish to communicate (receive data for Subscribers and send data for Publishers), they can only do so between those Subscribers 300 and/or Publishers 200 that support the same privacy level(s). Thus, the data shared between two participants is matched to a specific privacy level. For example, if Publisher (1) supports privacy levels A, B and C but Subscriber (1) only supports privacy level C, then Publisher A can only share data matching "C" privacy level with Subscriber (1). In some embodiments, Subscribers 300 can only view/create topics with privacy levels that they support. Similarly, Publisher Gateways 200g can be configured to publish only for topics at privacy levels that they support. Thus, in these embodiments, Subscribers 300 can only subscribe to data from Publishers 200 that support their privacy level. The Administrative Server 1100 can control the communications between the Publishers 200 and Subscribers 300 using the privacy levels for topics. The privacy levels can be maintained in a privacy level electronic register that can be associated with (incorporated into or communicate with) the Administrative Server 1100.

An organization 1000 may comprise a plurality of Publisher Gateways 200g, each having one or more different assigned privacy levels. While a privacy level for a Subscriber 300 defines what data that entity can receive, for a Publisher Gateway 200g, the respective privacy level(s) defines what data that Gateway 200g can send.

Figure 21A:
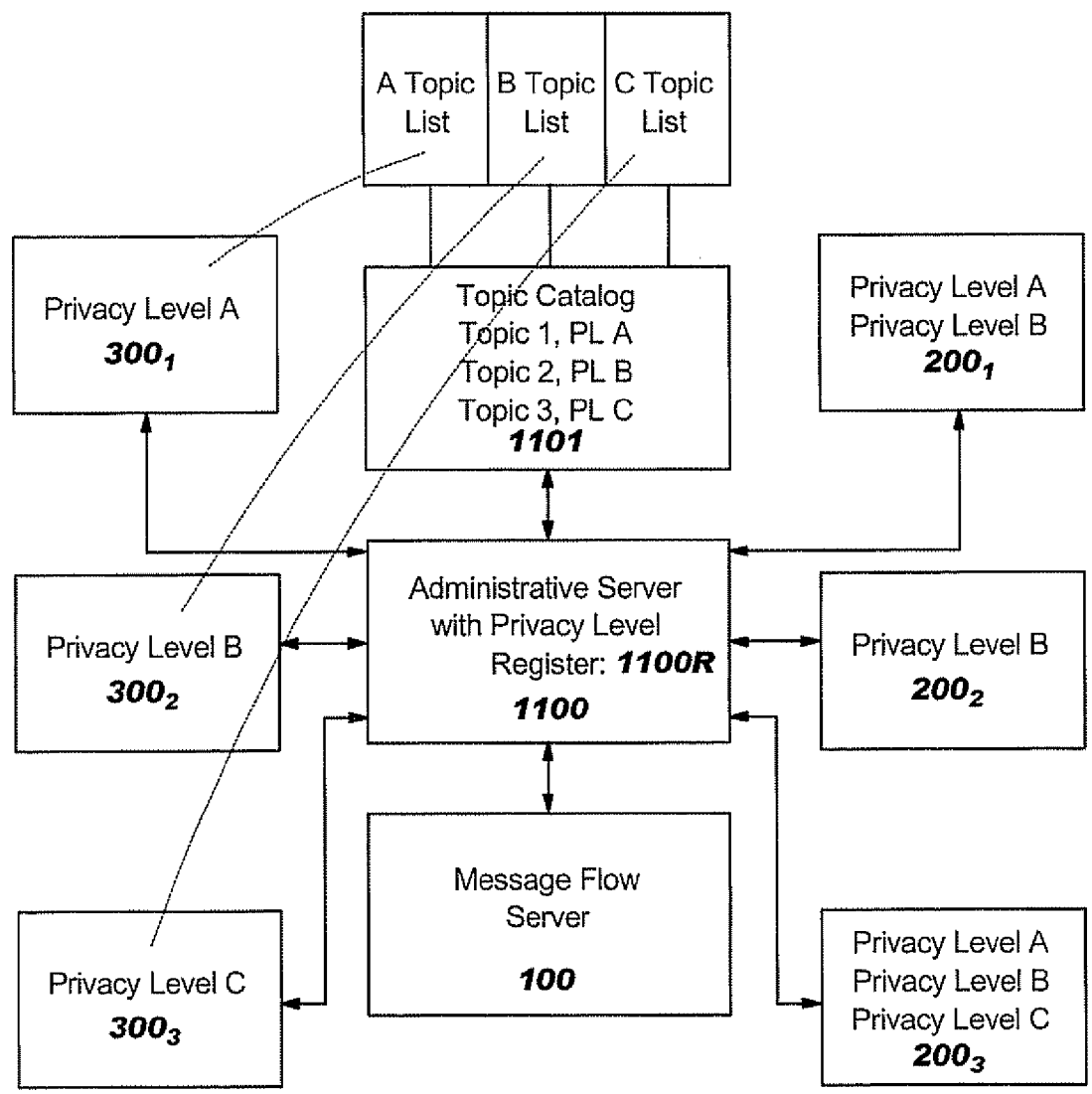
FIGS. 21A and 21B are block diagrams of examples of a computer network system of Subscribers and Publishers and topics having defined privacy levels according to embodiments of the present invention.
Figure 21B:
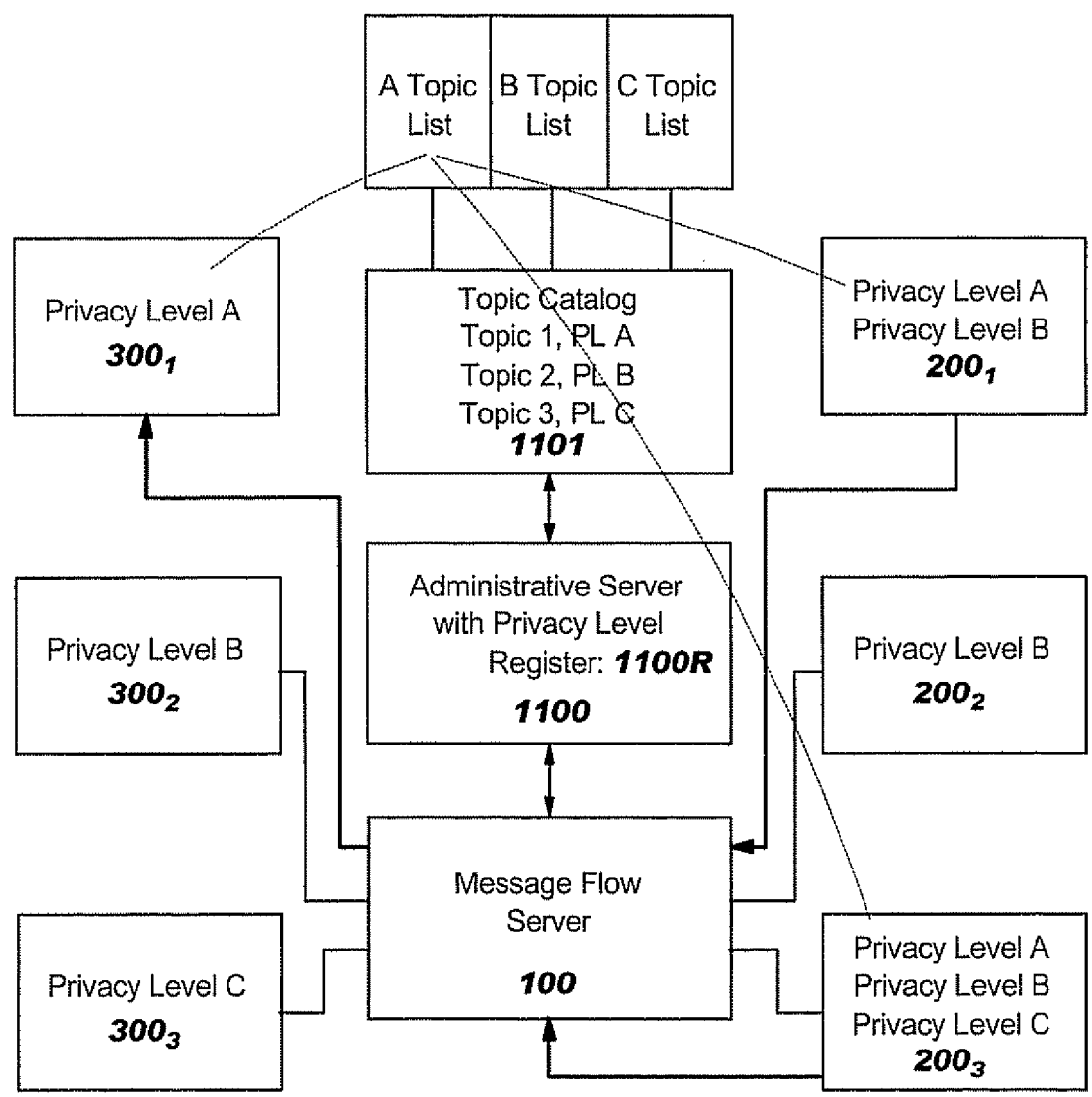

Referring to FIGS. 21A and 21B, three Subscribers $300_1$, $300_2$ and $300_3$ and three Publishers $200_1$, $200_2$, $200_3$ are shown in a data sharing system 10 as described above. As also described above, the system 10 can be configured to employ an electronic topic catalog 1101 each topic having an assigned privacy level (shown as "privacy level" ("PL") A, B and C, but greater or lesser privacy level categories may be used). Each Subscriber 300 can view, select and/or create a request for topics in the topic catalog 1101 that have a privacy level that matches that of the requesting, viewing or creating Subscriber. For example, as shown, Subscriber $300_1$ has a privacy level "A" and is able to view and/or create data topics in the catalog 1101 having an "A" privacy level. Similarly, if a "topic" is defined as a privacy level D topic, and a Subscriber 300 supports levels "A" and "D", the Subscriber 300 will only receive data at Level D. Similarly, if a Publisher 200 supports A, B and D, and desires to publish to the Level D topic, then the Publisher 200 can publish that topic. Publisher gateways 200g can publish to topics with privacy levels that their organization defines for them. If a Subscriber 300 or Publisher 200 wants to receive or publish data, respectively, to a topic at a different privacy level, a new topic will need to be specified at a privacy level that is supported by that entity. The supported privacy level can be described as an authorized "offering level" for a Publisher 200 and an "entitlement level" for a Subscriber 300. A Subscriber 300 can create a new topic with a supported privacy level but respective Publishers 200 can be configured to permissively publish (not required to publish) to the topic even if the privacy level is a supported privacy level.

The Administrative Server 1100 can communicate with and/or include an electronic privacy level Register 1100R which defines respective participants with corresponding privacy levels. Although shown in the box representing the Message Flow Server 100, in FIGS. 21A and 21B the Register 1100R can reside in and/or communicate with the Administrative Server 1100 or act as a stand alone module or component. The Register 1100R correlates a Subscriber 300 with a particular privacy level and acts to control communications between Subscribers 300 and Publishers 200 via the Message Flow Server 100 to inhibit or prevent access to non-authorized or non-entitled data from the Publishers 200. Examples of functional components of a Privacy Level Register 1100R are shown in FIG. 10, including one or more of the databases generally referred to as security directory 1103, and participant profiles 1102, and rules 1104. The Administrative Server 1100 can include and/or communicate with the Register 1100R as well as the topic catalog 1101 and the Message Flow Server 100 as described above so that only privacy level-entitled Subscribers 300 receive content specific data from Publishers 200.

As shown in FIGS. 21A and 21B, each Subscriber $300_1$-$300n$ (shown as $300_1$-$300_3$) has an assigned privacy level, which can be a global privacy level. In some embodiments, a Subscriber 300 and/or Publisher 200 may have more than one assigned privacy level. In some embodiments, the privacy level for a particular Subscriber 300 may be Publisher 200 specific. For example, where a Subscriber 300 is affiliated with a particular Publisher 200, a higher order privacy level (having an increased entitlement) may be assigned for that Publisher-Subscriber communication data sharing protocol.

FIG. 21A illustrates that a respective Subscriber 300 can view a subset of topics from a topic catalog 1101 via the portal (Administration Server or Web Application). The Administration Server communicates with all Subscribers and Publishers and the Message Flow Server 100. The communication flow between the Message Flow Server 100 and respective participants is not shown in FIG. 21A.

FIG. 21B illustrates that a Subscriber $300_1$ having a privacy level "A" can view and/or request a topic publication for those topics having an assigned "A" privacy level. Those Publishers that support privacy level "A" can receive the request and/or forward data matching that topic via the Message Flow Server 100. This communication protocol is shown by the dark, relatively thick, lines with arrows from Publishers $200_1$, $200_3$ to the Message Flow Server 100 then to Subscriber $300_1$.

Figure 22:
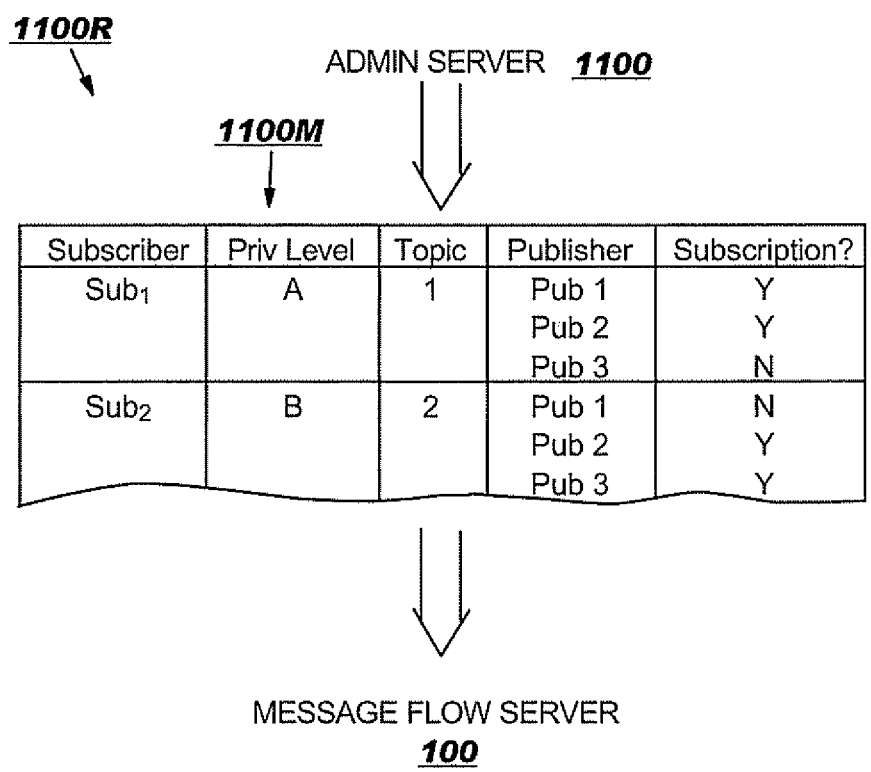
FIG. 22 is a schematic illustration of a compatibility correlation matrix that can be used to control data sharing between Subscribers and Publishers according to embodiments of the present invention.

FIG. 22 illustrates that the Privacy Level Register 1100R can comprise an electronic compatibility correlation matrix 1100M that can control the data sharing protocols between participating Subscribers and Publishers according to defined privacy level s of entitlement. The matrix 1100M can include data fields that define communication protocols/data content for each Subscriber 300 with respect to each Publisher 200 and may include a "Subscription" segment that confirms that a particular Publisher 200 has approved a subscription of their data for a topic, if that topic meets the privacy level. In operation, if a non-entitled Subscriber 300 attempts to obtain data, the Message Flow Server 100 will not forward the data from the Publisher 200 that has not approved this Subscriber for a "subscription" to their data on a particular selected topic and/or for a topic which is mis-matched to that Subscriber's privacy level. The Message Flow Server 100 can communicate with the Administrative Server 1100 and/or Privacy Register 1100R to verify the entitlement level of the Subscriber 300 for that topic and block access to that Publisher's data as appropriate.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for providing controlled levels of collaborative exchange of data using a hardware computer network of registered participating Subscribers and Publishers, comprising:
defining a set of different privacy levels, each privacy level having associated data sharing parameters that electronically control a participating Subscriber's ability to receive content specific data from each participating Publisher;
providing an electronic privacy level register that identifies for each participating Subscriber what the approved privacy levels are as selected from the set of different privacy levels with respect to each participating Publisher to thereby provide an entitlement based controlled electronic data sharing protocol between Subscribers and Publishers; and
providing an electronic topic catalog of health care topics, each topic having an assigned privacy level corresponding to one of the set of different privacy levels so that Subscribers can only request data for those topics at their respective privacy entitlement level and Publishers can only publish data for those topics at their privacy entitlement level.

2. A method according to claim 1, wherein the topic catalog is a global catalog of all selectable topics at all different privacy levels.

3. A method according to claim 2, wherein the Administrative Server is configured to display only those healthcare topics in the electronic topic catalog to a respective Subscriber at a respective web portal that correspond with a Subscriber's privacy level.

4. A method according to claim 1, wherein an Administrative Server Web Application communicates with the Message Flow Server to selectively forward Publisher healthcare data sent from Publishers only to entitled Subscribers based on Publisher-specific privacy levels defined in the privacy register for each Subscriber.

5. A method according to claim 4, wherein the privacy level registry comprises a compatibility correlation matrix that correlates a defined privacy level for each healthcare data topic for each Subscriber and for each Publisher.

6. A method according to claim 1, further comprising automatically electronically routing a Subscriber topic data request for a selected health care topic initiated by a Subscriber from the Administrative Server to one or more Publishers if the requesting Subscriber has a privacy level that entitles the Subscriber to have access to healthcare data from one or more Publishers.

7. A healthcare collaborative data sharing computer network system, comprising:
a Message Flow Server;
a plurality of Publisher participants having access to electronic patient healthcare records, each Publisher comprising at least one Publisher Gateway in communication with the Message Flow Server, wherein a respective Publisher Gateway is configured with at least one defined privacy level that electronically controls the Publisher Gateway's data sharing protocols with respective Subscribers;
plurality of Subscriber participants in communication with the Message Flow Server, each Subscriber having a defined privacy level that electronically controls their access to healthcare data from participating Publishers;
wherein healthcare data related to a healthcare topic is automatically selectively electronically forwarded to a Subscriber from a respective Publisher Gateway by the Message Flow Server only if the Subscriber has a privacy level that entitles the Subscriber to healthcare data for that topic.

8. A system according to claim 7, further comprising an Administrative Server in communication with an electronic user privacy register that defines a level of entitlement for different types of healthcare data for each Subscriber from each Publisher, wherein, in operation, electronic requests for healthcare data related to a healthcare topic are automatically electronically selectively forwarded to respective Publishers by the Administrative Flow Server only if a Subscriber has a privacy level that entitles the Subscriber to healthcare data for that topic.

9. A system according to claim 8, wherein the Administrative Server is configured to only electronically transmit requests for publication of health care data from a requesting Subscriber to those Publishers that have not disapproved publications to the requesting Subscriber.

10. A system according to claim 8, wherein the user privacy register comprises an electronic compatibility correlation database that correlates from a defined set of privacy levels, the privacy levels for different healthcare topics for each Publisher and each Subscriber, the system further comprising data sharing rules using the computer network with respect to each privacy level, the data sharing rules configured so that Publishers are compliant with healthcare privacy regulations.

11. A system according to claim 7, wherein the Subscribers are configured to be able to view an electronic topic catalog and select a healthcare topic from an electronic topic catalog associated with the privacy level of the respective Subscriber using a Web Application associated with the Administrative Server.

12. A method for providing controlled levels of collaborative exchange of data using a hardware computer network of registered participating Subscribers and Publishers, comprising:
  defining a set of different privacy levels, each privacy level having associated data sharing parameters that electronically control a participating Subscriber's ability to receive content specific data from each participating Publisher; and
  providing an electronic privacy level register that identifies for each participating Subscriber what the approved privacy levels are as selected from the set of different privacy levels with respect to each participating Publisher to thereby provide an entitlement based controlled electronic data sharing protocol between Subscribers and Publishers;
  wherein the plurality of different privacy levels comprise a first privacy level that allows only patient de-identified data to be shared between a Publisher and Subscriber and a second privacy level that allows limited patient data to be shared between a Publisher and Subscriber.

13. A method according to claim 12, further comprising a third privacy level that is non-restrictive as to data content between a Publisher and Subscriber.

14. A web-based secure data sharing system for providing and controlling collaborative healthcare data sharing between Publisher and Subscribe participants over the Internet, comprising:

a Message Flow Server configured to communicate with participant healthcare Publisher Gateways and Subscribers over the Internet; and
  an Administrative Server in communication with the Message Flow Server, the Administrative Server configured to control electronic communications between participating Subscribers and Publishers, wherein each participating Subscriber and Publisher has at least one defined privacy level selected from a defined set of privacy levels, wherein the Administrative Server is in communication with an electronic privacy level register that defines a privacy level for certain types of patient healthcare data, and wherein the system is configured to electronically control the communication between Subscribers and Publishers based on respective defined privacy level(s);
  wherein the Administrative Server communicates with respective Publishers and Subscribers and the Message Flow Server to selectively automatically electronically forward healthcare publication data for a respective topic received from Publishers to only those Subscribers entitled thereto based on a subscription thereto, the subscription being Subscriber and topic specific based on the privacy level associated with the topic of the healthcare data and the Subscriber privacy level for each Publisher.

15. A method for providing controlled levels of collaborative exchange of data using a hardware computer network of registered participating Subscribers and Publishers, comprising:
  defining a set of different privacy levels, each privacy level having associated data sharing parameters that electronically control a participating Subscriber's ability to receive content specific data from each participating Publisher;
  providing an electronic privacy level register that identifies for each participating Subscriber what the approved privacy levels are as selected from the set of different privacy levels with respect to each participating Publisher to thereby provide an entitlement based controlled electronic data sharing protocol between Subscribers and Publishers; and
  allowing a Subscriber to electronically select a topic of interest from an electronic topic catalog and electronically automatically trigger a request for publication of data related to the topic that is then sent over a computer network to participating Publishers having compliant privacy levels.

16. A method according to claim 15, further comprising allowing a Subscriber to electronically initiate a new topic data request with desired data constraints that is then automatically electronically stored in the topic catalog if the new topic data request has a privacy level that complies with the Subscriber privacy level.

* * * * *